(12) United States Patent
Fuchsberger et al.

(10) Patent No.: US 7,439,229 B2
(45) Date of Patent: Oct. 21, 2008

(54) CYTOKINE ACTIVITY REGULATOR MOLECULES FROM TICK SALIVARY GLANDS

(75) Inventors: Norbert Fuchsberger, Bratislava (SK); Valéria Hajnická, Bratislava (SK); Paula Kocáková, Bratislava (SK); Mirko Slovák, Bratislava (SK); Juraj Gašperík, Bratislava (SK)

(73) Assignee: Evolutec Limited, Reading, Berkshire (GB)

( * ) Notice: Subject to any disclaimer, the term of this patent is extended or adjusted under 35 U.S.C. 154(b) by 913 days.

(21) Appl. No.: 10/217,342

(22) Filed: Aug. 12, 2002

(65) Prior Publication Data

US 2003/0050244 A1 Mar. 13, 2003

Related U.S. Application Data

(63) Continuation of application No. PCT/GB01/00536, filed on Feb. 9, 2001.

(30) Foreign Application Priority Data

Feb. 11, 2000 (GB) .................................. 0003245.8
Dec. 22, 2000 (GB) .................................. 0031708.1

(51) Int. Cl.
*A61K 38/17* (2006.01)

(52) U.S. Cl. ..................... 514/12; 435/184; 435/320.1

(58) Field of Classification Search ....................... None
See application file for complete search history.

(56) References Cited

U.S. PATENT DOCUMENTS 5,811,514 A * 9/1998 Bard et al. .................. 530/324

FOREIGN PATENT DOCUMENTS

| WO | WO 95/04750 | * | 2/1995 |
| WO | WO 98/49303 | | 11/1998 |
| WO | WO 99/24567 | | 5/1999 |
| WO | WO 00/27873 | | 5/2000 |

OTHER PUBLICATIONS

Brown et al., Experimental Parasitology, 1986, vol. 62, pp. 40-50.*
Wang, et al., (1999), Molecular individuality: polymorphism of salivary gland proteins in three species of ixodid tick, Experimental and Applied Acarology, 23:969-975.
Brown and Askenase, (1986), Amblyomma americanum: Physiochemical Isolation of a Protein Derived from the Tick Salivary Gland that is Capable of Inducing Immune Resistance in Guinea Pigs, Experimental Parasitology, 62:40-50.
Yang, et al., (1999), Fully human anti-interleukin-8 monoclonal antibodies: potential therapeutics for the treatment of inflammatory disease states, Journal of Leukocyte Biology, 66:401-410.
Titus & Gillespie, (1999), T-Cell Activation and Signaling, Faseb Journal, 13:A954, Abstract No. 704.53, XP-000881956.

* cited by examiner

*Primary Examiner*—Christopher R. Tate
*Assistant Examiner*—Roy Teller
(74) *Attorney, Agent, or Firm*—Klauber & Jackson LLC

(57) ABSTRACT

The present invention relates to cytokine activity regulator molecules (CARMs) and their use in controlling the action of cytokines, particularly chemokines. In particular, the invention relates to CARMs that are derived from parasite salivary glands. The invention also relates to the use of CARMs in the treatment of diseases and allergies and in the production of vaccines that protect mammals, including humans, against the transmission of pathogenic (disease-causing) micro-organisms by certain parasites.

7 Claims, 20 Drawing Sheets

A) 100 pg IL-8
B) 85 pg MIP-1α
C) 60 pg RANTES
D) 80 pg MCP-1

A) 100 pg IL-8 (0.5 µl)
B) 85 pg MIP-1α (0.6 µl)
C) 60 pg RANTES (1.5 µl)
D) 60 pg MCP-1 (1.0 µl)

A) 100 pg IL-8 (5 µl)
B) 85 pg MIP-1α (15 µl)
C) 60 pg RANTES (15 µl)
D) 60 pg MCP-1 (15 µl)

A) 100 pg IL-8 (15 μl)
B) 85 pg MIP-1α (0,5 μl)
C) 60 pg RANTES (10 μl)
D) 80 pg MCP-1 (5 μl)

Fig. 9
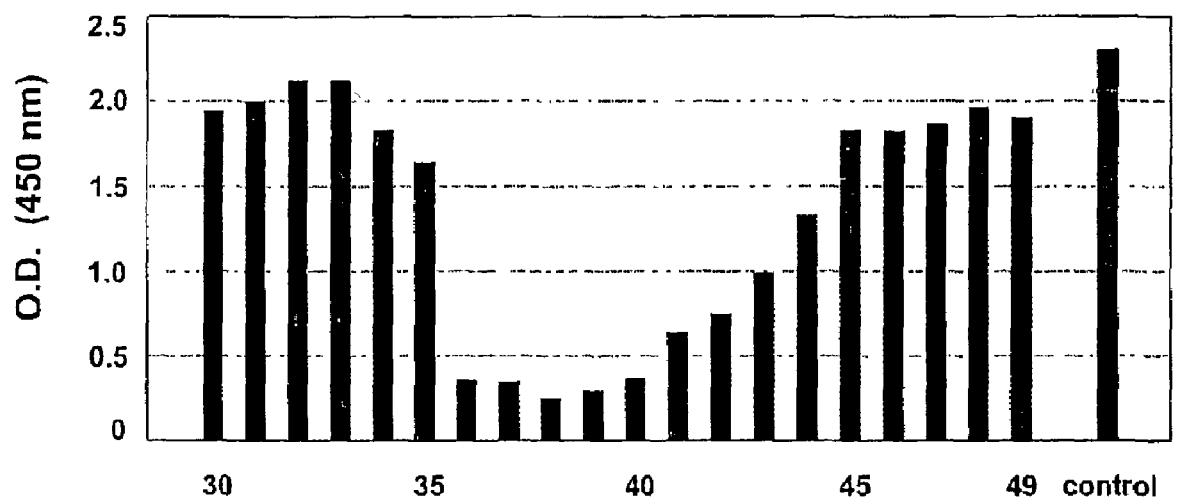
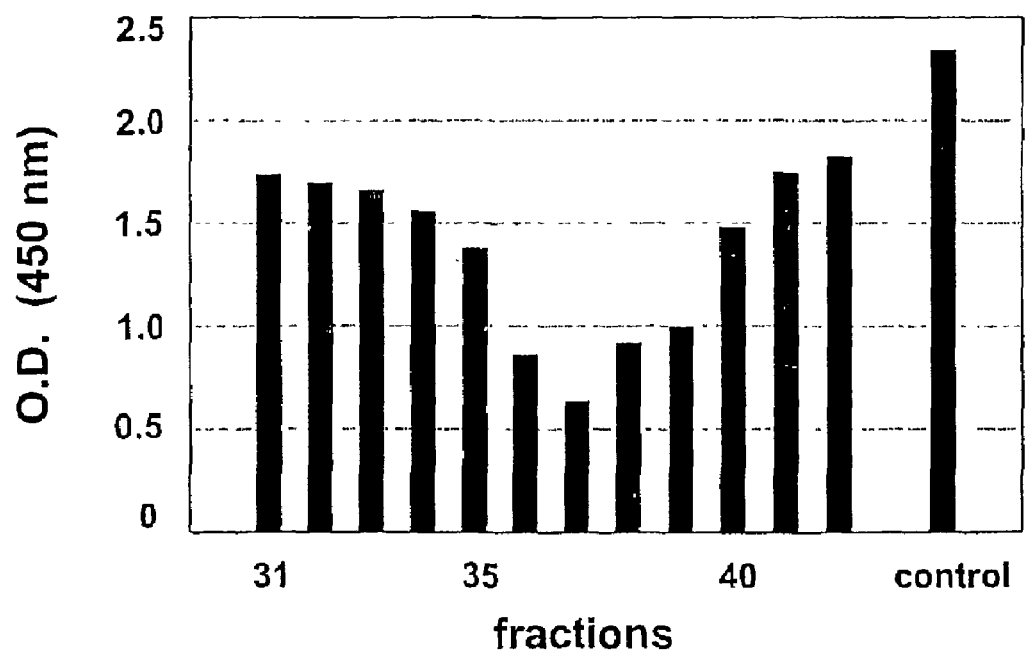
fractions control (■)  trypsin (▨) pretreated

A) Protein profile - control ——
   trypsin pretreated ——
B) 100 pg IL-8      (2.5 μl)
C) 120 pg MIP-1α    (10 μl)
D) 60 pg MCP-1      (10 μl)
E) 60 pg RANTES     (15 μl)

Fig. 15
A SDS-PAGE under reducing condition
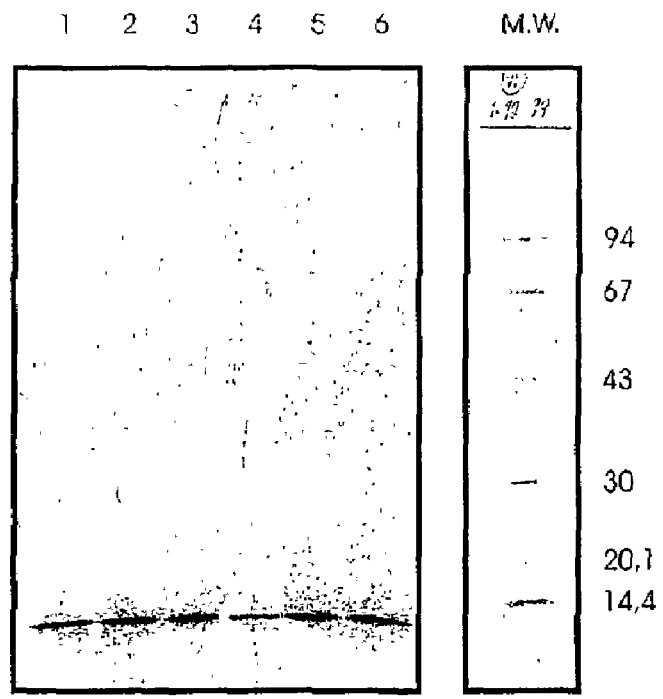
B SDS-PAGE under non-reducing condition
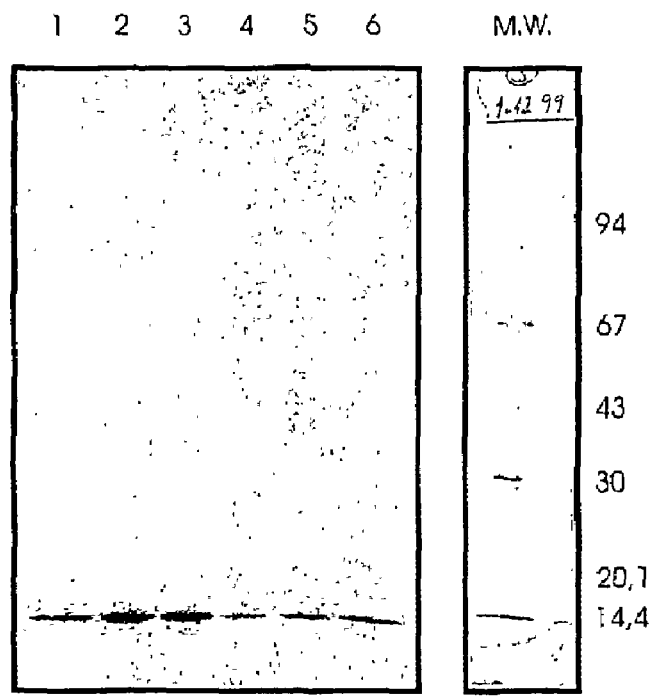

Fig. 20
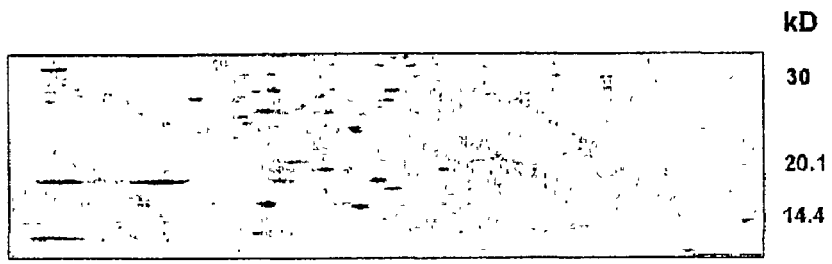
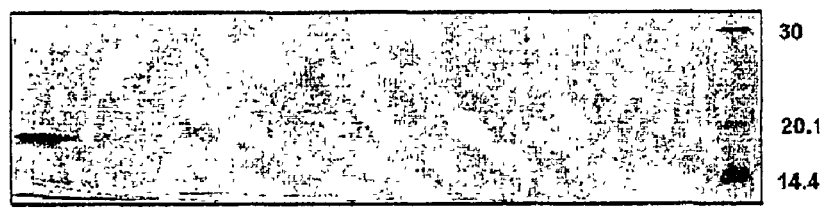
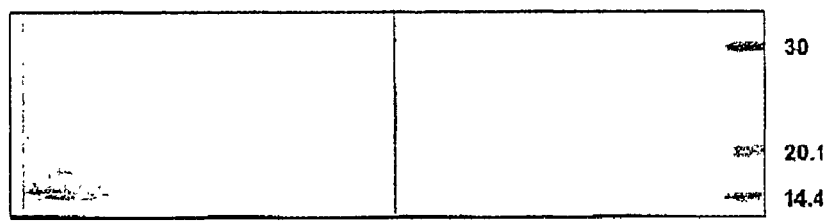
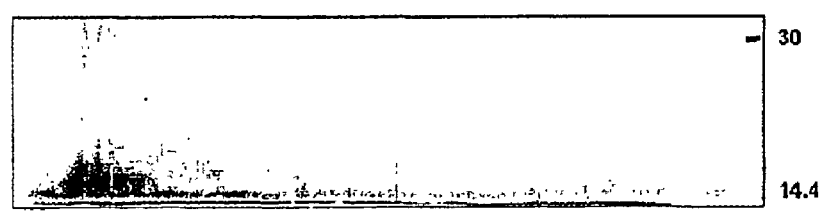

CYTOKINE ACTIVITY REGULATOR MOLECULES FROM TICK SALIVARY GLANDS

This application is a continuation of international application number PCTGB01/00536, filed Feb. 9, 2001.

The present invention relates to cytokine activity regulator molecules (CARMs) and their use in controlling the action of cytokines, particularly chemokines. In particular, the invention relates to CARMs that are derived from parasite salivary glands. The invention also relates to the use of CARMs in the treatment of diseases and allergies and in the production of vaccines that protect mammals, including humans, against the transmission of pathogenic (disease-causing) micro-organisms by certain parasites.

All documents mentioned in the text and listed at the end of this description are incorporated herein by reference.

Cytokines are peptides produced mainly by macrophages and lymphocytes, but also by other leukocytes, endothelial cells and fibroblasts. They function as regulators of inflammatory and immune reactions and some are involved in multiplication and differentiation of cells and their repair processes. Certain cytokines have an antiviral action. They are not produced constitutively, but are synthesised de novo on cell activation. Cytokines act on the target cell via specific, high-affinity receptors which, in most cases, are up-regulated in the cell when it is stimulated. Typically, the actions of cytokines are pleiotropic (one cytokine elicits several effects) and redundant (one action can be realised by different cytokines).

In addition to their own direct actions on cells, some cytokines induce the formation of other cytokines (which could constitute a necessary amplification cascade), some induce the receptors for other cytokines and some have complicated synergistic or antagonistic interactions with other cytokines. Cytokines have been likened to a complex signalling language with the final response of a particular cell involved being determined by a number of different messages received concurrently at the cell surface. The details of the functioning of this complex cytokine network are not yet fully understood. However, it is becoming clear that they are important pathophysiological mediators and have been shown to be implicated in the pathogenesis of numerous disease states.

Some cytokines belong to a family of closely-related proteins called chemokines. These small polypeptides are synthesised by phagocytes and by many other cell types. The chemokines function mainly as chemoattractants for leukocytes, recruiting monocytes, neutrophils and other effector cells from the blood to sites of infection. Some chemokines also function in lymphocyte development, migration and angiogenesis (the growth of new blood vessels).

Members of the chemokine family fall mostly into two broad groups—CC chemokines, with two adjacent cysteines, and CXC chemokines, in which the equivalent two cysteine residues are separated by another amino acid. The two groups of chemokines act on different sets of receptors and different cell types. In general, the CXC chemokines promote the migration of neutrophils whereas the CC chemokines promote the migration of monocytes or other cell types.

Interleukin-8 (IL-8) is an example of a CXC chemokine. An example of a CC chemokine is the monocyte chemoattractant protein-1 (MCP-1). These two chemokines have similar, although complementary, functions. IL-8 induces neutrophils to leave the bloodstream and migrate into the surrounding tissues. MCP-1, in contrast, acts on monocytes, inducing their migration from the bloodstream to become tissue macrophages. Other CC chemokines such as RANTES may promote the infiltration into tissues of a range of leukocyte cell types, including effector T cells, with individual chemokines acting on different subsets of cells.

A few chemokines do not fall within these two categories. The only known C chemokine is called lymphotactin and is thought to attract T-cell precursors to the thymus. A newly discovered molecule called fractalkine has three amino acid residues between the two half-cysteines, making it a $CX_3C$ chemokine. It is multimodular and it is tethered to the membrane of cells that express it, where it serves both as a chemoattractant and as an adhesion protein.

The role of chemokines such as IL-8 and MCP-1 in cell recruitment is twofold. First, to convert the initial rolling of the leukocyte on the endothelial cells into stable binding and second to direct its migration along a gradient of the chemokine that increases in concentration towards the site of infection. This is achieved by the binding of the small, soluble chemokines to proteoglycan molecules in the extracellular matrix and on endothelial cell surfaces, thus displaying the chemokines on a solid substrate along which the leukocytes can migrate. Once the leukocytes have crossed the endothelium and the basement membrane to enter the tissues, their migration to the focus of infection is directed by the gradient of matrix-associated chemokine molecules.

Both IL-8 and MCP-1 also activate their respective target cells, so that not only are neutrophils and macrophages brought to potential sites of infection but, in the process, they are armed to deal with any pathogens that they may encounter. In particular, neutrophils exposed to IL-8 and TNF-α are activated to mediate a respiratory burst, that generates oxygen radicals and nitric oxide, and to release their stored granule contents, thus contributing both to host defence and to local tissue destruction seen in local sites of infection with pyogenic (pus-forming) bacteria.

The central role of chemokines in inflammatory reactions has been demonstrated by numerous studies including the suppression of chemokines by treatment with neutralising antibodies. For example, neutralising antibodies to IL-8 suppress acute inflammatory reactions due to reperfusion injury, endotoxin-induced arthritis, endotoxin-provoked subcutaneous inflammations and acute glomerulonephritis (Harrada, A. et al., 1994). Antibodies to the CC chemokine, macrophage inflammatory protein (MIP-1α), reduce the severity of experimental autoimmune encephalomyelitis (EAE) in mice. Additionally, deletion of the MIP-1α gene in mice reduces the severity of post-Coxsackie-induced myocarditis, but also decreases the resistance of such mice to influenza infection (Cook, 1996), implying that MIP-1α may promote antiviral host defences.

Just as all the chemokines have similar structures, all their receptors are similar in structure. All are integral membrane proteins containing seven membrane-spanning helices. This structure is characteristic of receptors such as rhodopsin and the muscarinic acetylcholine receptor, which are coupled to guanine nucleotide binding proteins (G-proteins). The chemokine receptors are also activated through coupled G-proteins.

The main pathophysiological effects of cytokines result from inappropriate or prolonged production of cytokines. Thus, certain cytokines are implicated in sepsis, rheumatoid arthritis, inflammatory bowel disease, glomerulonephritis, psoriasis, acute and chronic myelogenous leukaemia, insulin-dependent diabetes melitus, melanoma, osteoporosis, atherosclerosis and graft versus host rejection. The pathogenesis of several other autoimmune diseases, such as autoimmune thyroiditis, has also been linked to certain cytokines.

Given the important role of cytokine and chemokine activity in this wide range of diseases, there is currently great interest in the development and use of effective antagonists of cytokines (Schwarz & Wells, 1999a; Schwarz & Wells 1999b; Zack et al, 1999). Such antagonists, for example soluble receptors, are useful in studies on the effects of specific cytokines produced de novo in humans and domestic animals and are likely to find application in controlling the adverse effects of inappropriate or prolonged production of particular cytokines.

There are some known immunomodulatory molecules that inhibit the actions of cytokines. In particular, several viruses produce proteins that block the actions of cytokines by binding to cytokines (so-called 'soluble receptors') such that the cytokine can no longer bind with its cell receptor (Alcami & Smith, 1995; Alcami et al, 1998).

A study by Wikel et al 1994 suggested that ticks may produce a bioactive molecule that inhibits the production or elaboration of certain cytokines. Preparations from the salivary glands of *Dermacentor andersoni* ticks appeared to suppress elaboration of TNF, interleukin-1, interleukin-2 and interferon-γ by lymphocytes and macrophages in vitro. However, it is not clear whether it is possible to isolate this or any other cytokine inhibitor, or exactly what activity such an inhibitor might possess. For instance, inhibition of the expression or production of cytokines is useless for most therapeutic, diagnostic and research applications. What is urgently required in these fields is an antagonist of cytokine action. Currently there are relatively few cytokine antagonists on the market and their potential as therapeutic agents has thus not been thoroughly explored.

Evidence has been reported that ticks may produce molecules that block cytokine receptors (Hajnicka et al, 2000) but the nature of such postulated molecules is unknown. Furthermore, there is no suggestion by Wikel et al, 1994 or Hajnicka et al, 2000 that ticks, or any other macroparasite, may produce soluble factors that bind to cytokines and thus inhibit their activity. Given the importance of cytokines in mammalian disease and allergic response, there thus remains an urgent need for effective inhibitors of cytokines. Novel molecules have now been discovered in macroparasites that are capable of antagonising the action of cytokines.

SUMMARY OF THE INVENTION

According to a first aspect of the present invention, there is provided a cytokine activity regulator molecule (CARM) derived from a macroparasite, or a variant or a functional equivalent of a CARM, that specifically inhibits the action of a cytokine.

By "cytokine activity regulator molecule" is meant any molecule that specifically binds to a cytokine or to a receptor for a cytokine, thereby inhibiting its action.

Inhibitors of cytokine action that have been described previously include viral proteins-such as p35 of vaccinia virus that has high affinity for CC chemokines (Alcami et al 1998). Apart from viral cytokine regulators, all other inhibitors of cytokine activity are either antibodies to cytokines or cytokine receptors, peptide antagonists (including truncations and amino terminal extensions or modifications of chemokines) and nonpeptidic small molecule antagonists.

The CARMs according to the invention are potent inhibitors of the action of cytokines and are unrelated to the known immunomodulatory molecules discussed above. The CARMs of the present invention are introduced into a mammalian host animal from a macroparasite and function as regulators of the action of specific cytokines. In the case of blood-feeding ectoparasites, these molecules are hypothesised to antagonise cytokine actions that would otherwise impair parasite feeding. This function derives from the ability of the CARMs to block the action of specific cytokines. The CARMs of the invention may inhibit the action of cytokines by binding to the cytokine itself, or to its receptor(s), thereby preventing it from performing its intended protective function.

Preferably, the CARMs of the present invention inhibit the action of chemokines, such as CC or CXC cytokines. Particularly preferred CC cytokines include RANTES, MCP-1,2,3,4 or 5, Eotaxin, and most preferably MIP-1α. Particularly preferred CXC chemokines include GCP-2, GRO, NAP-2, IP-10, Mig and most preferably IL-8.

The CARMs of the present invention are derived from macroparasites, namely any parasite that does not reproduce directly within its definitive host (Anderson & May, 1991). The term "macroparasite" includes blood-feeding parasites, including blood-feeding ectoparasites, such as ticks, horseflies, mosquitoes, sandflies, blackflies and leeches, blood-sucking bats, and endoparasites, such as hookworms. Other examples of macroparasites will be clear to those of skill in the art.

Preferably, the CARMs of the present invention are derived from blood-feeding ectoparasites, such as ticks or blood-sucking bats. Preferably, they are derived from ticks, most preferably from the tick species *Dermacentor reticulatus, Rhipicephalus appendiculatus, Amblyomma variegatum, Haemaphysalis inermis* or *Ixodes ricinus*.

In one aspect of the invention, a CARM which is active against cytokines has a molecular weight of approximately 14 to 20 kDa, preferably approximately 14 kDa.

The invention further provides that CARMs that form multimeric complexes, such as homodimers or heterodimers.

A further aspect of the invention provides that CARMs are resistant to trypsin.

The term "functional equivalent" is used herein to describe derivatives or fragments of CARMs or of molecules belonging to the same family as the CARMs that retain the capacity to inhibit the action of cytokines or that contain epitopes which can be used in the development of vaccines that target members of the CARM family. Functional equivalents of the CARMs of the present invention include natural biological variants (e.g. allelic variants or geographical variations within the species from which the CARMs are derived). This term also refers to molecules that are structurally similar to the CARMs of the present invention or that contain similar or identical tertiary structure. Such functional equivalents may be derived from native CARMs or they may be prepared synthetically or using techniques of genetic engineering. In particular, synthetic molecules that are designed to mimic the tertiary structure or active site of the CARMs are considered to be functional equivalents. Fragments of the functional equivalents as defined above are themselves included in the term "functional equivalent".

Variants of CARMs may include, for example, mutants containing amino acid substitutions, insertions or deletions from the wild type sequence. Variants with improved function from that of the wild type sequence may also be designed through the systematic or directed mutation of specific residues in the protein sequence. Improvements in function that may be desired will include greater specificity or affinity for the target cytokine or cytokine receptor.

Derivatives of the molecules, variants and functional equivalents described above are also included as embodiments of the invention. Such derivatives may include one or more additional peptides or polypeptides fused at the aminoor carboxy-terminus of the CARMs. The purpose of the additional peptide or polypeptide may be to aid detection, expression, separation or purification of the protein or it may lend the protein additional properties as desired. Examples of potential fusion partners include beta-galactosidase, glutathione-S-transferase, luciferase, a polyhistidine tag, a T7 polymerase fragment and a secretion signal peptide. Such derivatives may be prepared by genetically or chemically fusing the peptides.

It is considered that the proteins, variants and functional equivalents of the invention may be prepared in recombinant form by expression in a host cell. Such expression methods are well known to those of skill in the art and many are described in detail by Sambrook et al (1989) and Fernandez & Hoeffler (1998).

The proteins, variants and functional equivalents of the present invention can also be prepared using conventional techniques of protein chemistry. For example, protein fragments may be prepared by chemical synthesis, a technique that is especially useful for the generation of peptide fragments of CARMs, for use as immunogens.

According to a further aspect of the invention, there is provided a nucleic acid molecule comprising a nucleotide sequence encoding a CARM, a fragment or functional equivalent thereof according to the above-described aspects of the invention. Such molecules include single- or double-stranded DNA, cDNA and RNA, as well as synthetic nucleic acid species. Preferably, the nucleic acid sequences comprise DNA.

The invention also includes cloning and expression vectors containing the DNA sequences of this aspect of the invention. Such expression vectors may incorporate the appropriate transcriptional and translational control sequences, for example enhancer elements, promoter-operator regions, termination stop sequences, mRNA stability sequences, start and stop codons or ribosomal binding sites, linked in frame with the nucleic acid molecules of the invention.

Additionally, it may be convenient to cause a recombinant protein to be secreted from certain hosts. Accordingly, further components of such vectors may include nucleic acid sequences encoding secretion, signalling and processing sequences.

Vectors according to the invention include plasmids and viruses (including both bacteriophage and eukaryotic viruses), as well as other linear or circular DNA carriers, such as those employing transposable elements or homologous recombination technology. Many such vectors and expression systems are known and documented in the art (Fernandez & Hoeffler, 1998). Particularly suitable viral vectors include baculovirus-, adenovirus- and vaccinia virus-based vectors.

Suitable hosts for recombinant expression include commonly used prokaryotic species, such as E. coli, or eukaryotic yeasts that can be made to express high levels of recombinant proteins and that can easily be grown in large quantities. Mammalian cell lines grown in vitro are also suitable, particularly when using virus-driven expression systems. Another suitable expression system is the baculovirus expression system that involves the use of insect cells as hosts. An expression system may also constitute host cells that have the DNA incorporated into their genome. Proteins, or protein fragments may also be expressed in vivo, for example in insect larvae or in mammalian tissues.

A variety of techniques may be used to introduce the vectors according to the present invention into prokaryotic or eukaryotic cells. Suitable transformation or transfection techniques are well described in the literature (Sambrook et al, 1989; Ausubel et al, 1991; Spector, Goldman & Leinwald, 1998). In eukaryotic cells, expression systems may either be transient (e.g. episomal) or permanent (chromosomal integration) according to the needs of the system.

The invention also includes transformed or transfected prokaryotic or eukaryotic host cells containing a nucleic acid sequence as defined above.

A further aspect of the invention provides a method for preparing a CARM, a fragment or functional equivalent of the invention, as defined above, which comprises culturing a host cell containing a nucleic acid according to the invention under conditions whereby said protein is expressed and recovering said protein thus produced.

A further aspect of the invention provides a method for isolating a CARM comprising the steps of: preparing an extract from a macroparasite as defined previously; separating said extract into fractions of differing molecular weight; testing said fractions for the ability to inhibit a cytokine; and isolating said CARM from a fraction(s) that possesses the ability to inhibit cytokine activity.

Preferably, said extract is a salivary gland extract. The preparation of such salivary gland extracts may take place at several different points in the feeding cycle. In a preferred embodiment of this aspect of the invention, salivary gland extract is prepared from an adult female or male tick that has been feeding for five days or more.

Preferably, said macroparasite is a blood-feeding ectoparasite or an endoparasite. More preferably, it is derived from a tick or a blood-sucking bat. Preferably, it is derived from ticks, most preferable from the tick species *Dermacentor reticulatus, Rhipicephalus appendiculatus, Amblyomma variegatum, Haemaphysalis inermis* or *Ixodes ricinus*.

Methods of separating macroparasite extracts into fractions of differing molecular weight will be well known to those skilled in the art. Preferably, such separation may be carried-out using a chromatographic procedure, such as fast phase liquid chromatography, high-performance liquid chromatography (HPLC), anion exchange chromatography or reverse phase HPLC.

Testing of said fractions for their ability to inhibit a cytokine can also be carried out by methods known to those skilled in the art. Preferably, such fractions are tested using an enzyme linked immunosorbent assay (ELISA) or radiolabelled cytokine binding as set out in the examples given herein.

Following identification of fractions that possess the ability to inhibit cytokine activity, a CARM may be isolated by any suitable procedure such as SDS-polyacrylamide gel electrophoresis or two dimensional gel electrophoresis.

A CARM obtainable using a method set out above may optionally be sequenced using methods well known to those skilled in the art.

The present invention includes a CARM obtainable by the above method. Preferably, the CARM isolated regulates the activity of chemokines, such as IL-8, MIP-1α, MCP-1, RANTES, IP-10 or eotaxin.

In a particularly preferred embodiment of the invention, a CARM is obtained by a method comprising the steps of:
  a) preparing a salivary gland extract from a tick;
  b) separating said extract into fractions of differing molecular weight;
  c) testing said fractions for the ability to inhibit the activity of a cytokine; and
  d) isolating said CARM from a fraction(s) that possesses the ability to inhibit cytokine activity.

The present invention also provides methods of isolating a gene encoding a CARM isolated using any of the above methods. The isolated protein may be subjected to amino acid sequencing followed by screening of salivary gland gene libraries using the polymerase chain reaction to isolate the gene encoding the CARM. An example of a suitable procedure is screening of cDNA libraries, optionally cDNA expression libraries. Certain expression libraries can be designed to generate tagged proteins, so facilitating their analysis and purification. Similar procedures for the preparation and isolation of parasite proteins can be found in co-owned patent applications PCT/GB97/01372 and PCT/GB98/03397. A variety of procedures for isolating the gene encoding the CARM will be known to the person skilled in the art.

In a particularly preferred embodiment of the invention, a gene encoding the CARM is obtained by a method comprising performing the steps outlined in detail above to isolate the CARM and additionally performing the steps of:

e) obtaining the N-terminal sequence of said isolated CARM;
f) designing a degenerate oligonucleotide; and
g) using said oligonucleotide to screen a salivary gland gene library to isolate a gene encoding the CARM.

Once the CARM has been isolated, sequencing of the N-terminal can be carried out by methods known to those skilled in the art. Following the determination of the N-terminal peptide sequence of the CARM, the skilled person will readily be able to design one or more degenerate oligonucleotide probes or degenerate PCR primers which could encode this peptide sequence. These are then used to screen a salivary gland gene library by hybridisation or PCR. Preferably, such a library is a cDNA gene library.

According to a further aspect of the invention there is provided a composition comprising a CARM, variant or functional equivalent according to the above-described aspects of the invention in conjunction with a pharmaceutically acceptable carrier.

Pharmaceutically-acceptable carriers include any carrier that does not itself induce the production of antibodies harmful to the individual receiving the composition. Suitable carriers are typically large, slowly metabolised molecules such as proteins, polysaccharides, polylactic acids, polyglycolic acids, polymeric amino acids, amino acid copolymers, lipid aggregates (such as oil droplets or liposomes) and inactive virus particles. Such carriers are well known to those of skill in the art.

The composition may be used as a vaccine and may thus optionally comprise an immunostimulating agent, for instance an adjuvant referred to above. According to a further aspect of the invention, there is provided a process for the formulation of a vaccine composition comprising bringing a protein, protein fragment or functional equivalent according to the above-described aspects of the invention into association with a pharmaceutically-acceptable carrier, optionally with an adjuvant. Suitable adjuvants are well-known in the art and include oil-in-water emulsion formulations, saponin adjuvants, Complete Freund's Adjuvant (CFA) and Incomplete Freund's Adjuvant (IFA) and other substances that act as immunostimulating agents to enhance the effectiveness of the composition.

According to a further aspect, the present invention provides for use of CARMs, variants or functional equivalents thereof to bind or otherwise destroy specific cytokines or specific cell receptors in animals, thereby regulating the actions of specific cytokines and controlling their pathological effects. Preferably, such animals are mammals, more preferably humans or domesticated mammals.

The invention also provides a method of treating an animal suffering from a cytokine-mediated disease or condition, comprising administering to said animal a CARM, a fragment or functional equivalent or a pharmaceutical composition according to the above-described aspects of the invention in a therapeutically effective amount. Preferably, said animal is a mammal, more preferably a human.

Preferably, said disease is an autoimmune disease such as sepsis, rheumatoid arthritis, inflammatory bowel disease, glomerulonephritis, psoriasis, acute and chronic myelogenous leukaemia, insulin-dependent diabetes melitus, melanoma, osteoporosis, atherosclerosis autoimmune thyroiditis or graft versus host rejection.

According to a still further aspect of the present invention, there is provided a method of vaccinating an animal against a disease or condition, comprising administering to said mammal a CARM, a fragment or functional equivalent or a pharmaceutical composition according to the above-described aspects of the invention.

Metazoan parasites, particularly arthropods and helminths, are sources of infectious diseases and other injurious effects that have major impacts in human and veterinary medicine. Control of the arthropod and helminth parasites currently relies primarily on the use of chemicals such as acaricides and antihelmintics. Attempts have been made to use immunological means of control through the use of vaccine technology. There has been some success in identifying certain protective antigens of metazoan parasites as potential vaccine candidates, but only a few have as yet come to commercial fruition, most notably for the cattle lungworm *Dictyocaulus viviparous* and the cattle tick *Boophilus microplus*.

An alternative vaccine strategy is to use antigens that protect against the infections transmitted by metazoan parasites, for which the metazoan parasites act as vectors. For example, the yellow fever vaccine is used to protect humans against infection by the mosquito-transmitted yellow fever virus. The disadvantage of using vaccines that control vector-transmitted diseases is that different vaccines are usually required to protect against each disease. Thus vaccines that control disease vectors (such as ticks and mosquitoes) have the added advantage of controlling several different infections transmitted by one (or a number of related) disease vector(s).

Despite these developments, there is nonetheless a continuing need for metazoan parasite vaccines and in particular for a vaccine which may be used across a broad range of arthropod and/or helminth genera.

It is also known that the saliva of metazoan disease vectors, such as ticks and sandflies, promotes the transmission of certain infections from the disease vectors to the animal hosts on which they feed (Nuttall et al, 1994). This process has been named saliva-activated transmission (SAT). Vaccines that target SAT factors, such as CARMs, have the advantage both of controlling the disease vector and inhibiting the transmission of vector-borne infections (so-called transmission-blocking vaccines). There is a need to identify suitable immunogens for development as transmission-blocking vaccines.

A further aspect of the present invention therefore provides for the use of CARMs, variants, functional equivalents or fragments or a pharmaceutical composition, as defined above, as immunogens for use as metazoan parasite vaccines and in particular as protective immunogens in the control of diseases caused by infections transmitted by arthropods and other metazoan parasites. Suitable candidates for vaccination include humans and domesticated animals such as cattle, goats, sheep, dogs, cats and other animals which require protection against metazoan parasites, especially ticks, and the infections they transmit. The vaccine may be administered singly, or in combination with other immunogens. Infections which may be treated or prevented by such compositions include East Coast fever, babesiosis, cowdriosis, Nairobi sheep disease, tick-borne encephalitis, Lyme disease, dengue fever, yellow fever, leishmaniasis and malaria.

The present invention also includes the use of CARMs as tools in the study of cytokine-regulated immunity or other physiological effects of cytokines such as their role in inflammation and in auto-immune diseases. For example, the CARMs may be used for paralysing the action of IL-8 in cell cultures or in animal tissues in vitro in order to study the importance of IL-8 in these systems.

Various aspects and embodiments of the present invention will now be described in more detail by way of example, with particular reference to CARMs isolated from ticks, and especially from *Dermacentor reticulatus* and *Amblyomma variegatum*. It will be appreciated that modification of detail may be made without departing from the scope of the invention.

BRIEF DESCRIPTION OF FIGURES

FIG. 9 shows the anti-eotaxin activity of FPLC fractions of SGE derived from (A) *Amblyomma variegatum* male ticks (0.5 µl fractions) and (B) *Dermacentor reticulatus* male ticks (1 µl fractions) using 80 pg per treatment of eotaxin, detected by ELISA.

FIG. 15 shows cross-linking of $^{125}$I-IL-8 to selected FPLC fractions of SGE derived from *D. reticulatus* adult females fed for 5 days. Sodium dodecyl sulphate-polyacrylamide gel electrophoresis (SDS-PAGE) run under either reducing (A) conditions with β-mercaptoethanol, or non-reducing (B) conditions i.e. without β-mercaptoethanol. Samples in lanes 1 to 3 were not cross-linked whereas samples in lanes 4 to 6 were cross-linked with DTSSP. Lane 1=$^{125}$I-IL-8; lane 2=$^{125}$I-IL-8+fraction 35; lane 3=$^{125}$I-IL-8+fraction 41; lane 4=$^{125}$I-IL-8; lane 5=$^{125}$I-IL-8+fraction 35; lane 6=$^{125}$I-IL-8+fraction 41; M.W.=molecular weight markers.

FIG. 20 shows the results of 2D gel electrophoresis of: A SGE prepared from *D. reticulatus* females ticks fed for 5 days, (B) FPLC fractions 37+38 of *D. reticulatus* females ticks fed for 5 days, (C) FPLC fractions 42+43 of *D. reticulatus* females ticks fed for 5 days, (D) FPLC fraction 41 of *D. reticulatus* females ticks fed for 5 days (stained with Coomassie blue), (E) saliva prepared from *A. variegatum* female ticks fed for 10 days, and (F) SGE of from *A. variegatum* female ticks fed for 10 days.

EXAMPLES

Materials and Methods

Preparation of Tick Salivary Gland Extract (SGE)

*Dermacentor reticulatus* and *Ixodes ricinus* ticks were collected by flagging the vegetation in selected localities of western Slovakia. All other tick species examined were obtained from laboratory colonies (Jones et al, 1988). Adult ticks were allowed to feed on Balb-C or ICR female mice, or guinea pigs, as described previously (Kubes et al, 1994). After the specified number of days of feeding, female ticks were gently removed from the animals and their salivary glands dissected out on ice, washed with saline, and homogenised in pools of salivary glands in a final volume of 10 µl per tick. The protein concentration of the clarified supernatant was determined using the Bradford method (Bradford, 1976). Samples were dried using a Speed-Vac, stored at 4° C., and rehydrated prior to use.

Fractionation of Tick SGE by Fast Phase Liquid Chromatography (FPLC)

Figure 1:
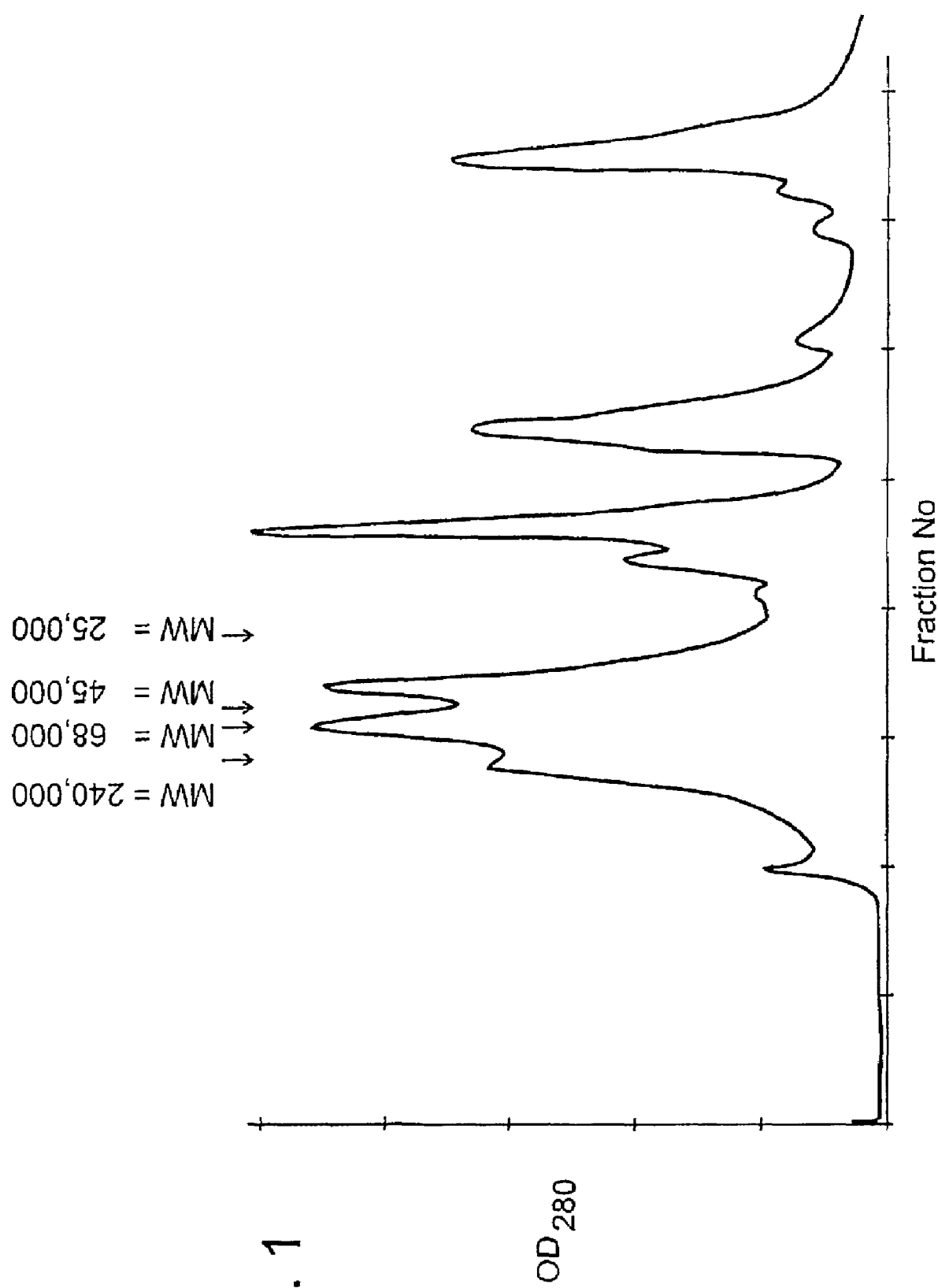
FIG. 1 shows the fractionation of salivary gland extract (SGE) of *Dermacentor reticulatus* adult female ticks fed for 5 days using fast phase liquid chromatography (FPLC). Arrows indicate the positions of molecular weight markers (Boehringer).

Pooled SGE preparations that had been dried using a Speed-Vac and stored in eppendorf tubes in 1200 to 5000 µg amounts were solubilised by adding to each eppendorf sample 30 µl 0.02 M Tris HCl pH 7.5. After being held for 60 min at 5° C., the suspension was centrifuged 10 min×15,000 g. The sediments were re-extracted 3 times and then all four preparations were pooled and then centrifuged 10 min at 15,000 g. The supernatant (100 µl) was separated by liquid chromatography under native conditions at 5° C. using a Superose 12 HR10/30 column (Pharmacia) with an equilibrium buffer of 0.02 M Tris HCl, 0.15 M NaCl, pH 7.5, and a sample volume of 100 µl, flow rate of 0.4 ml/min and one fraction collected per min. An example of the separation of SGE derived from *D. reticulatus* adult females fed for 5 days is shown in FIG. 1.

Detection of IL-8 by Enzyme-linked Immunoabsorbent Assay (ELISA)

The IL-8/Nap-1 ELISA Bender MedSystems kit (Cat. No. BMS204MS) was used, with recombinant human interleukin-8 (72 amino acids) from Research Diagnostics Inc., USA (Cat. No. RDI-208M). The IL-8 was prepared by dissolving 25 µg (1 ampoule) in 1 ml 0.1% bovine serum albumin. Five µl aliquots were stored at −70° C. (5 µl=125 ng IL-8). Before the test, IL-8 was diluted in Leibowitz medium supplemented with 5% of bovine serum and mixed for 2 hr at room temperature with the test sample (SGE or FPLC fractions of SGE) by gentle shaking. Aliquots of 50 µl containing a final concentration of about 100 pg of IL-8 and 5 µl of test sample per well were applied in duplicate to the ELISA plate. Washing and optical density measurements were carried out using a DYNATECH LABORATORIES apparatus.

Detection of Chemokines other than IL-8 by Enzyme-linked Immunoabsorbent Assay (ELISA).

Human chemokines were detected using specific ELISA kits according to the manufacture's instructions. Kits were from R&D Sytems (Quantikine® Assays), Abingdon, U.K.: MIP-1α (Cat. No. DMA00), RANTES (Cat. No. DRN00), MPC-1 (Cat. No. DCP00), and Eotaxin (Cat. No. DTX00). For each assay, 110 µl chemokine were mixed with 10 µl of SGE or FPLC fractions of SGE in eppendorf tubes. Each mixture was incubated 2 hr at room temperature by gentle shaking. Duplicate 50 µl aliquots were applied to the ELISA plate. Washing and optical density (O.D.) measurements at 450 nm were carried out using a Dynatech Laboratories apparatus. Human IP-10 was detected using an R&D ELISA Development System comprising human IP-10 as the standard (Cat. No. 266-IP-010), capture antibody (Cat. No. MAB266), and detection antibody (Cat. No. BAF266).

Treatment of SGE with Trypsin 5.2 mg SGE were dissolved in 420 µl of 0.02M Tris pH 7.5 and divided into 2 aliquots, one untreated (control) and the second treated with trypsin at a final concentration of 1%. The aliquots were incubated for 2 hrs at 37° C. and then 200 µl of each fractionated by FPLC. A combination of two columns was used (Superose 12 and then Superdex 75) in tandem. The columns were eluted with 0.02M TRIS HCl pH 7.5, 0.15 M NaCl at a flow rate of 0.4 ml per minute and one fraction collected per 1.5 min.

2D-polyacrylamide Gel Electrophoresis (PAGE)

Dried SGE or FPLC fractions were dissolved in buffer containing 9M urea and 4% Triton X-100 as described previously (Dunbar, 1987). The isoelectric focusing was performed in tubes in gels prepared with 2% ampholines pH 3-10 (SERVALYTE). Then 25 µl of each sample containing 2% β-mercaptoethanol and 2% ampholines were loaded per gel. Samples were focused at 12 kV-h. For the second dimension, SDS-polyacrylamide gels with a linear gradient of 7.5-12.5% acrylamide were used. After separation, gels were silver stained.

Protein Electrophoretic Blotting

Proteins resolved by 2D-PAGE were transferred overnight at 100 mA in Towbin transfer buffer (25 mM Tris, 192 mM glycine, 20% methanol, pH 8.3) to a PVDF membrane. Transferred proteins were visualized by staining with Coomassie blue.

Sodium Dodecyl Sulphate-polyacrylamide Gel Electrophoresis (SDS-PAGE)

SDS-PAGE with discontinuous buffers was carried out in a gradient of 7.5 to 12.5% polyacrylamide in 1.5 mm thick gels (Laemmli, 1979) in reducing or non-reducing conditions (with or without β-mercaptoethanol, respectively).

Example 1

Effect of Tick SGE on the Detection of IL-8 Produced by the Human Monocytic Leukaemia Cell Line, THP-1

The human monocytic leukaemia cell line, THP-1, was obtained from the German Collection of Microorganisms and Cell Cultures, Germany. The cells were grown in RPMI-1640 medium supplemented with 10% foetal bovine serum, 100 U/ml penicillin, 100 µg/ml streptomycin, and 0.25 µg/ml amphotericin B at 37° C. in a humidified atmosphere containing 5% $CO_2$.

Figure 2:
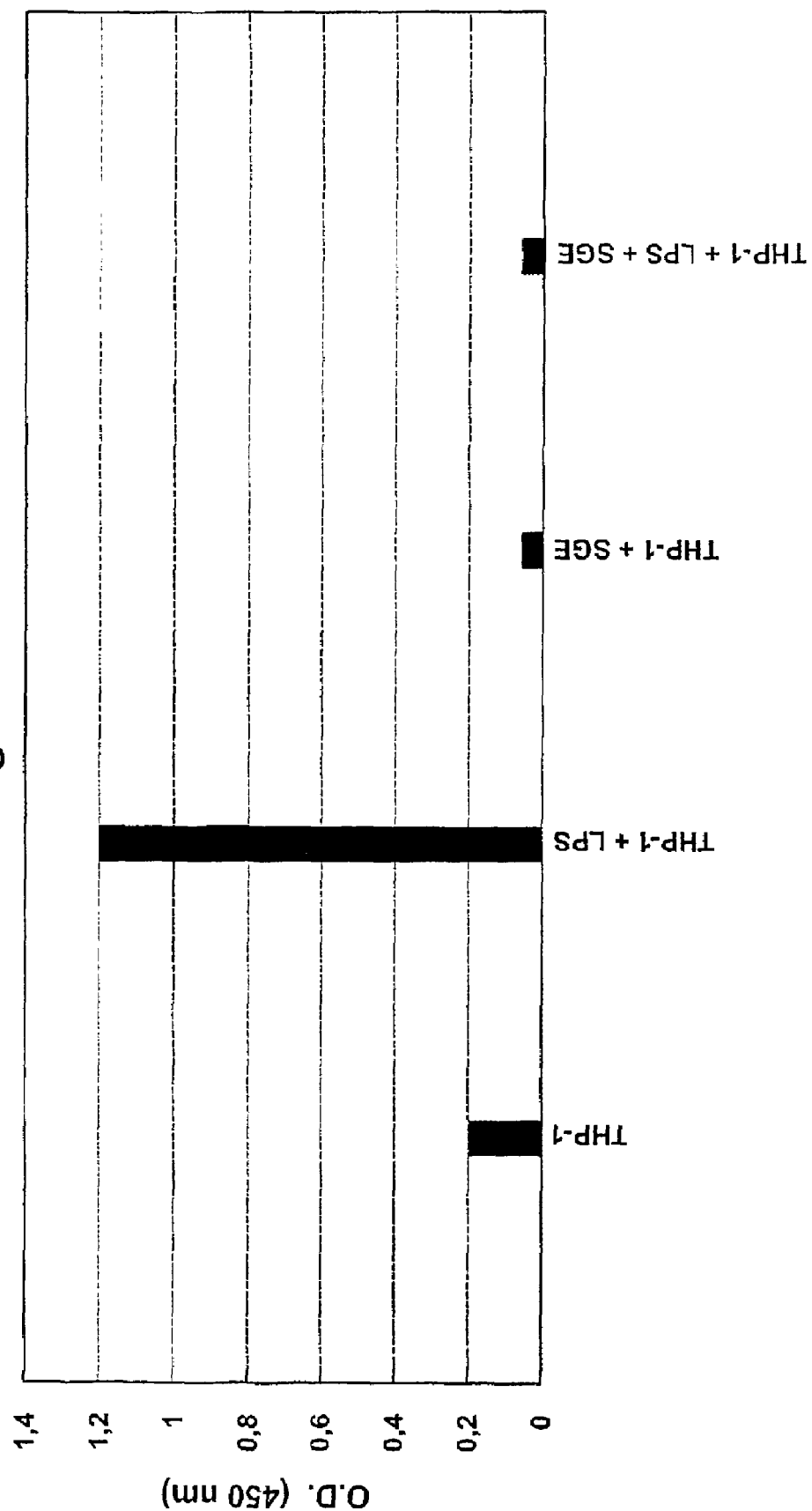
FIG. 2 shows the effect of tick SGE on IL-8 production by the human monocytic leukemic cell line, THP-1, measured by enzyme linked immunoabsorbent assay (ELISA). LPS=lipopolysaccharide; SGE from *D. reticulatus* adult females fed for 5 days.

When the cells were treated with lipopolysaccharide (LPS) from *E. coli* serotype 026:B6 (SIGMA-ALDRICH CHEMIE GmbH), a high level of IL-8 was detected by ELISA (FIG. 2). A low level of IL-8 was detected for cells not stimulated with LPS.

In the presence of SGE from *D. reticulatus* adult females fed for 5 days, using either LPS-stimulated or unstimulated (no LPS) THP-1 cells, the amount of IL-8 detected by ELISA was reduced to levels comparable to those of the control blank (0.06) indicating that no IL-8 was detectable.

Example 2

Comparison of Treatment with SGE Derived from Different Tick Species on the Detection of IL-8

100 pg human recombinant IL-8 were incubated for 2 hr with 5.5 µg SGE derived from various ixodid tick species (*D. reticulatus, A. variegatum, I. Ricinus, H. inermis* and *R. appendiculatus*). The amount of IL-8 was then measured by ELISA.

Figure 3:
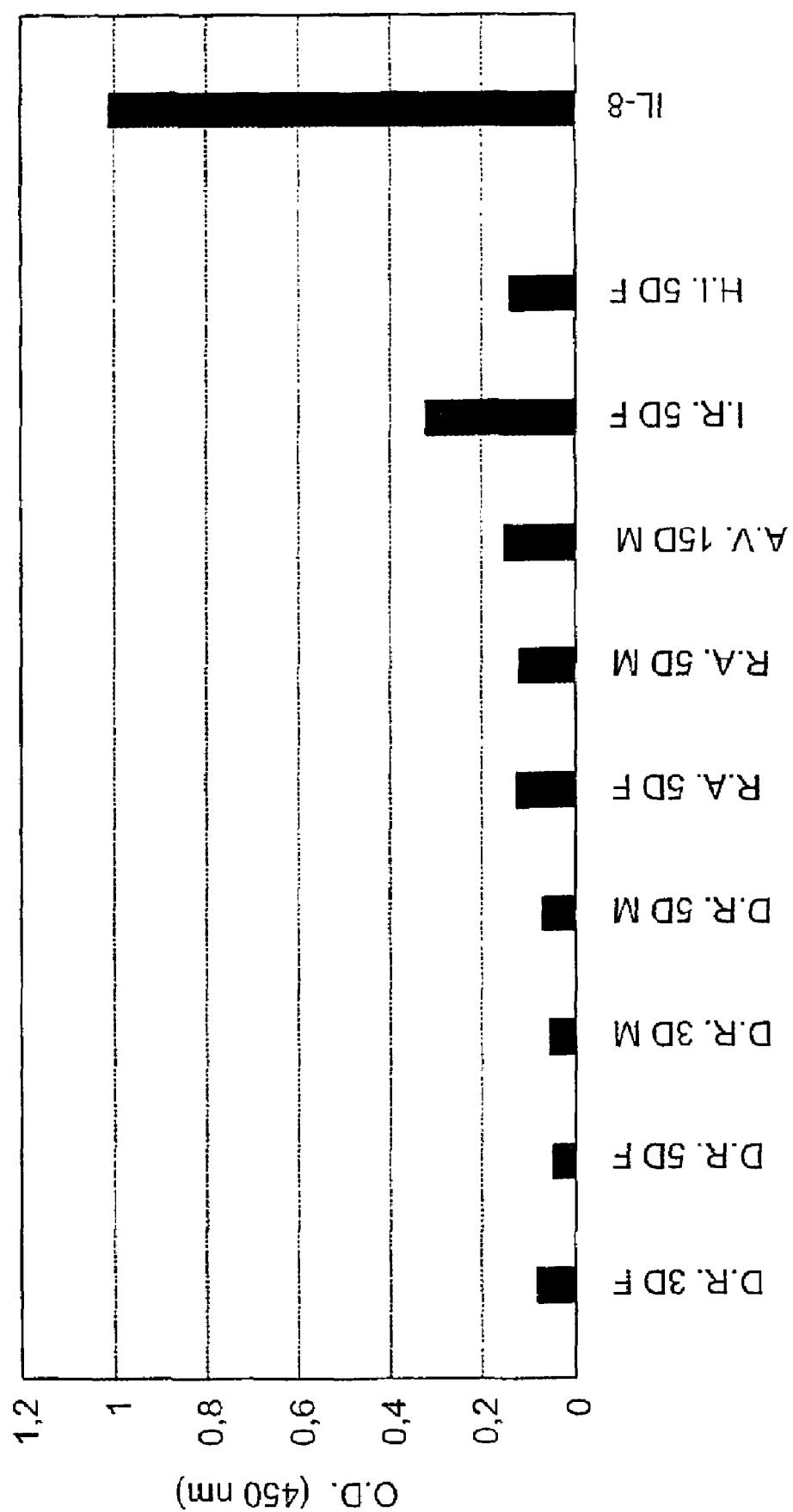
FIG. 3 shows the detection by ELISA of 100 pg of IL-8 after 2 hours incubation with SGE from different tick species. D.R. 3D F=*Dermacentor reticulatus* adult females fed for 3 days; D.R. 5D F=*D. reticulatus* adult females fed for 5 days; D.R. 3D M=*D. reticulatus* adult males fed for 3 days; D.R. 5D M=*D. reticulatus* adult males fed for 5 days; R.A. 5D F=*Rhipicephalus appendiculatus* adult females fed for 5 days; R.A. 5D M=*R. appendiculatus* adult males fed for 5 days; A.V. 15D M=*Amblyomma variegatum* adult males fed for 15 days; I.R. 5D F=*Ixodes ricinus* adult females fed for 5 days; H.I. 5D F=*Haemaphysalis inermis* adult females fed for 5 days; IL-8=IL-8 alone not treated with SGE.

FIG. 3 shows that the amount of detectable IL-8 was reduced significantly by treatment tick SGE. The greatest reduction occurred with SGE from *D. reticulatus* adult females fed for 5 days.

Example 3

Effect of FPLC Fractions of *D. reticulatus* SGE on the Level of IL-8, MIP-1α, RANTES and MCP-1

Figure 4:
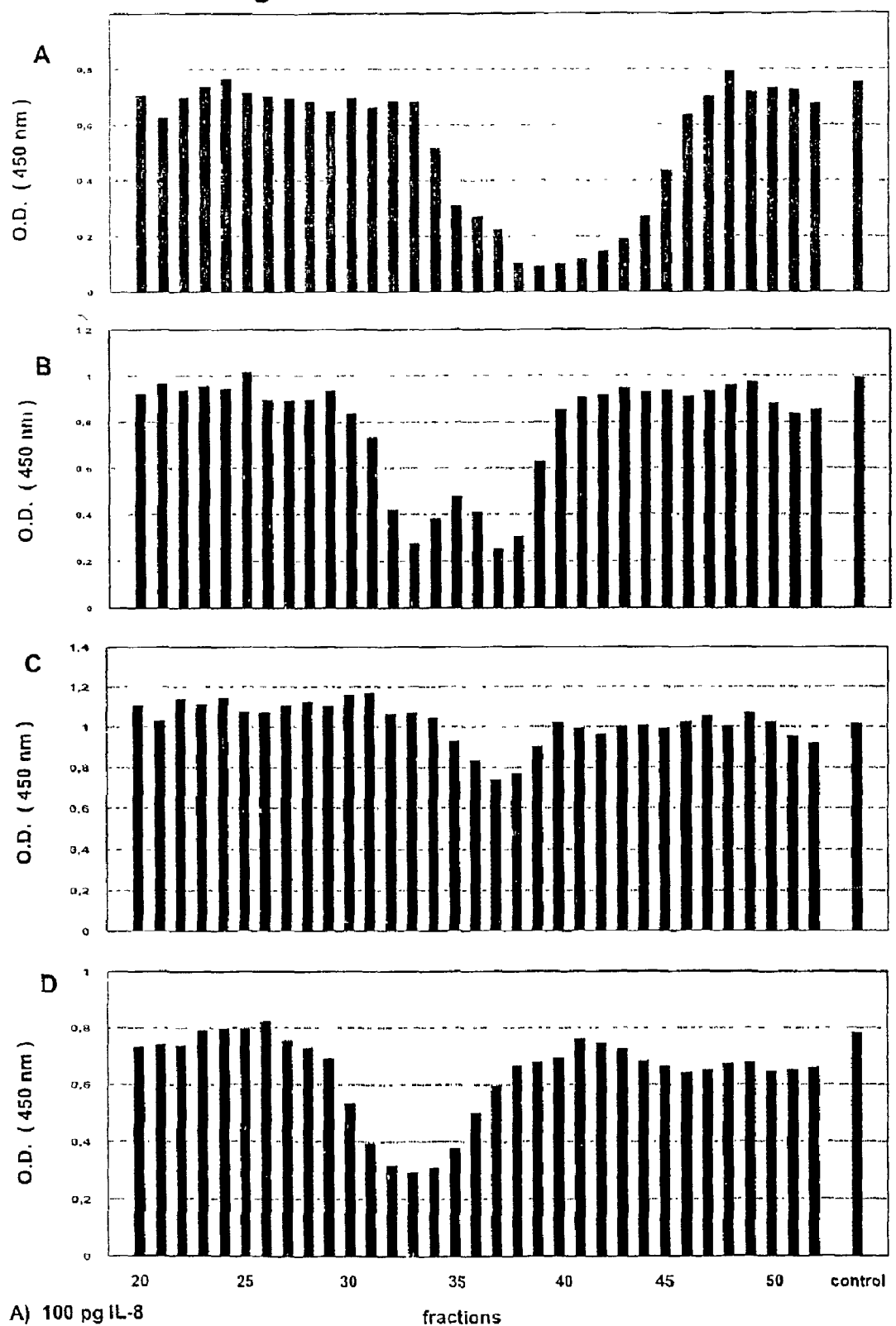
FIG. 4 shows the anti-chemokine activity of FPLC fractions (1 µl) of SGE derived from 5 days fed *Dermacentor reticulatus* female ticks (174 ticks; 4.12 mg proteins) detected by ELISA.
Figure 5:
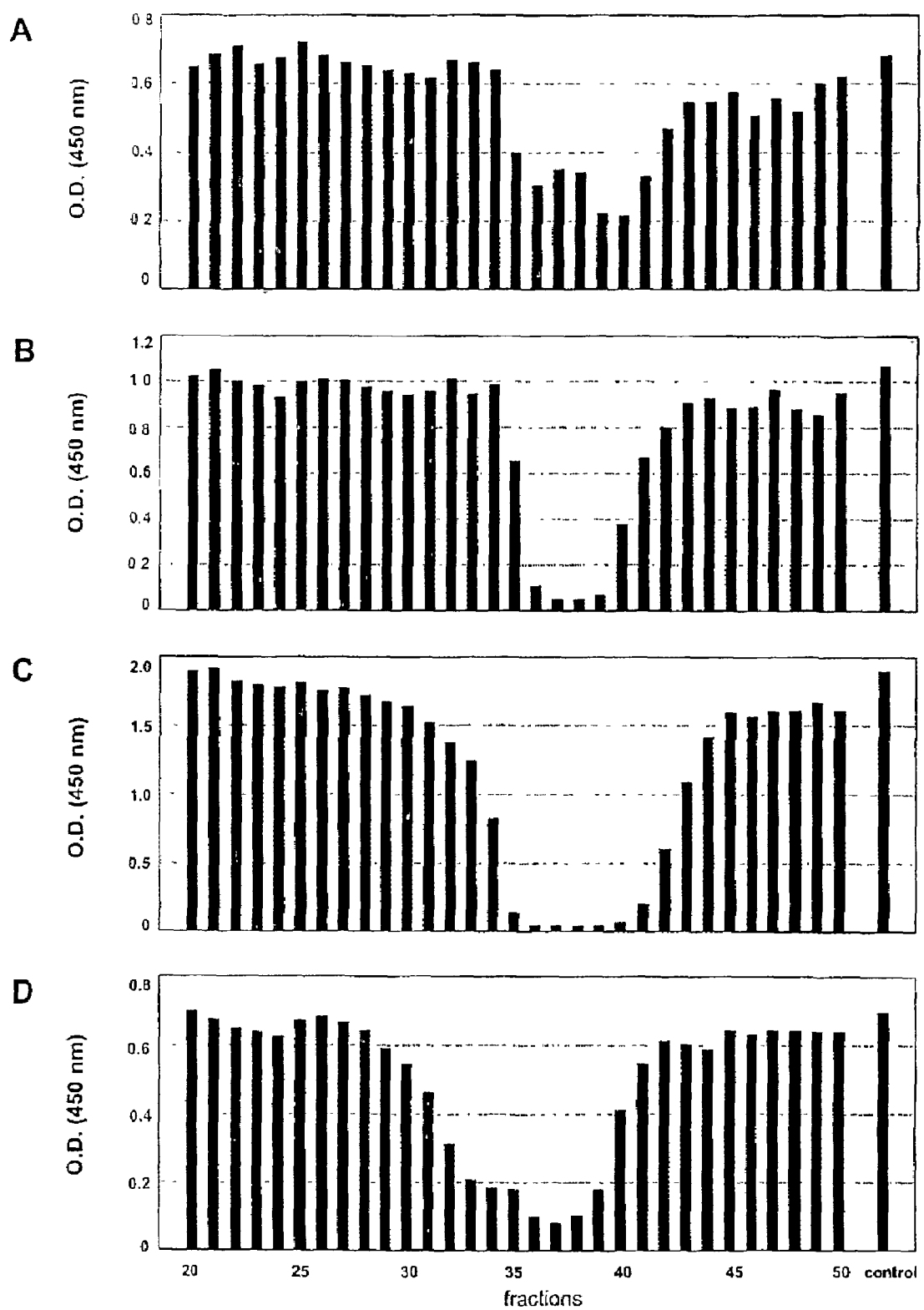
FIG. 5 shows the anti-chemokine activity of FPLC fractions (400 µl) of SGE derived from 5 to 6 days fed *Dermacentor reticulatus* male ticks (522 ticks; 3.3 mg proteins) detected by ELISA.

Human recombinant chemokines (100 pg IL-8, 85 pg MIP-1α, 60 pg RANTES or 80 pg MCP-1) were incubated for 2 hr with 1 µl FPLC fractions of SGE derived from either *D. reticulatus* females (174 ticks; 4.12 mg proteins) or males (522 ticks; 3.3 mg proteins) fed for 5 or 6 days. The amount of chemokine was then measured by ELISA. A reduction in optical density (O.D.) indicates a reduction in the level of detectable chemokine. FIGS. 4 and 5 show that the fractionated SGE of female and male ticks, respectively, contains two peaks of anti-IL-8 activity (the female peaks overlap), two peaks for females and one peak for males against MIP-1α, one anti-RANTES peak, and two overlapping peaks for male and one for female to MCP-1. Alignment of the peaks of activity indicate the presence of at least three different tick anti-chemokine molecules.

Example 4

Effect of FPLC Fractions of *R. appendiculatus* SGE on the Level of IL-8, MIP-1α, RANTES and MCP-1

Figure 6:
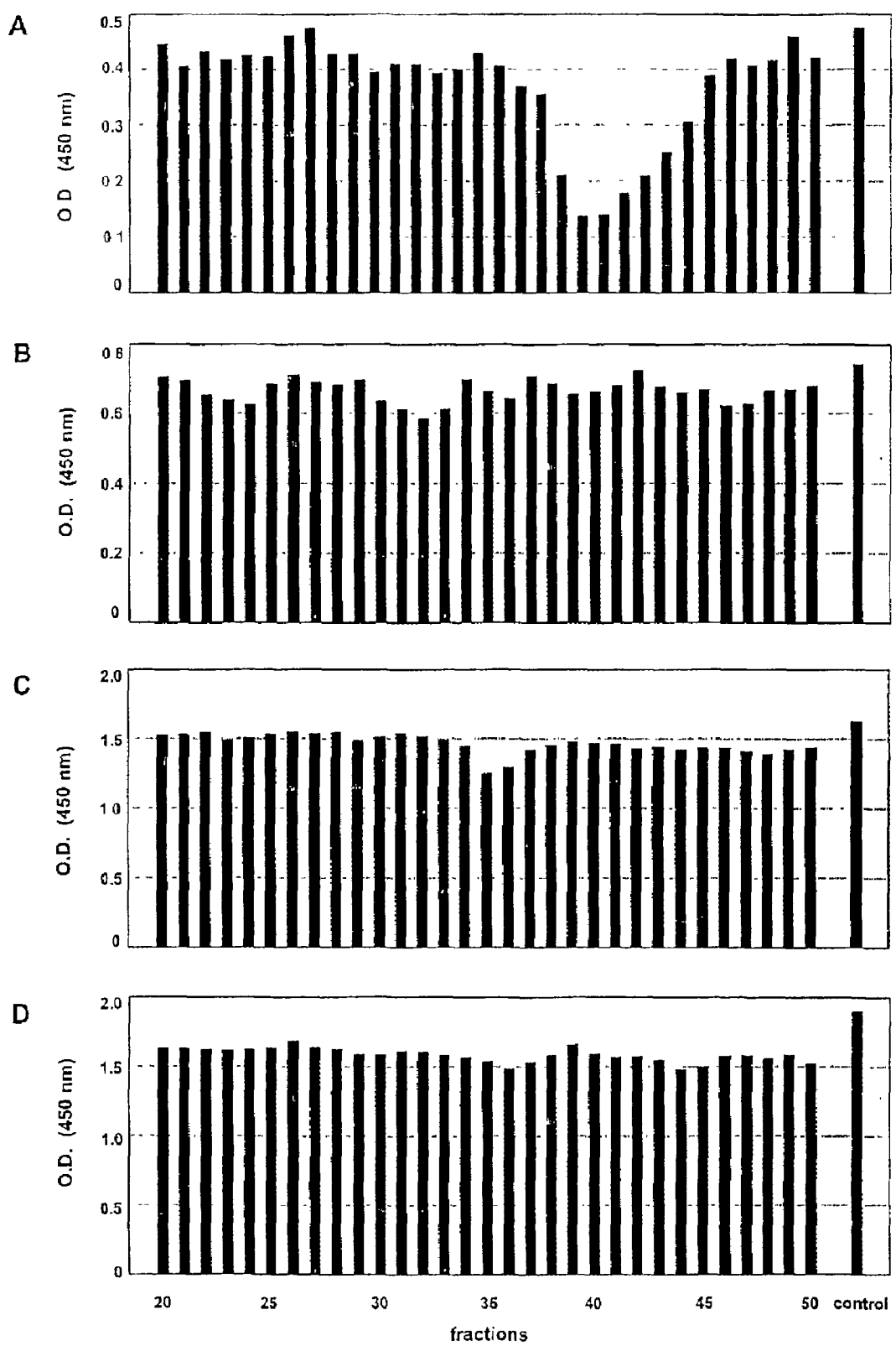
FIG. 6 shows the anti-chemokine activity of FPLC fractions (400 µl) of SGE derived from 5 to 6 days fed *Rhipicephalus appendiculatus* female ticks (121 ticks; 1.966 mg proteins) detected by ELISA.

The method used in Example 3 was repeated using FPLC fractions of SGE from *R. appendiculatus* adult females fed for 5 days (121 ticks; 1.966 mg proteins). In contrast to *D. reticulatus* (Example 3), only one peak of anti-IL-8 activity, which included fractions 40 and 41, was detected (FIG. 6). No activity to the other chemokines was apparent.

Example 5

Effect of FPLC Fractions of *A. variegatum* SGE on the Level of IL-8, MIP-1α, RANTES and MCP-1

Figure 7:
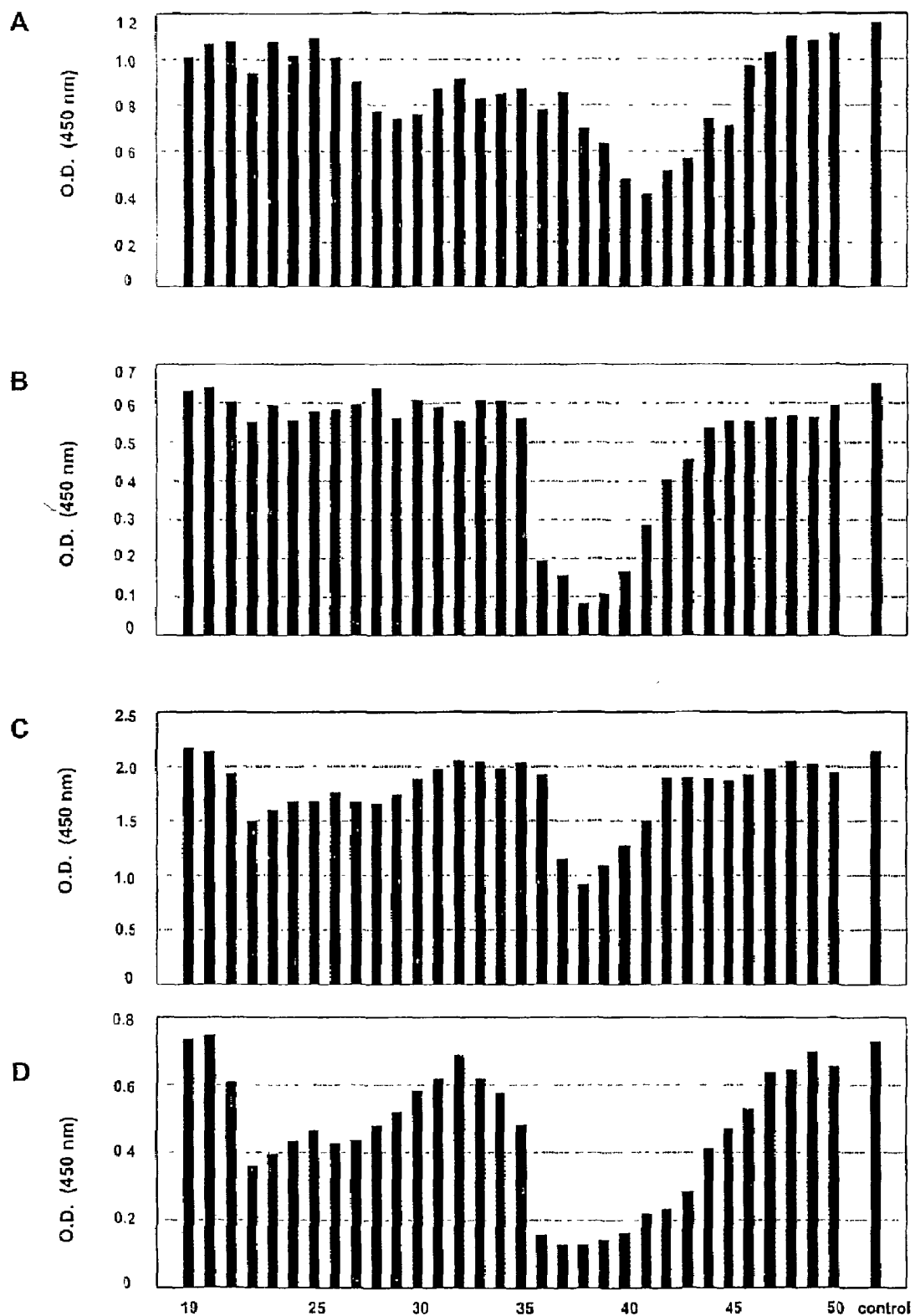
FIG. 7 shows the anti-chemokine activity of FPLC fractions (400 µl) of SGE derived from 11 to 12 days fed *Amblyomma variegatum* male ticks (65 ticks; 2.39 mg proteins) detected by ELISA.

The method used in Example 3 was repeated using FPLC fractions of SGE from *A. variegatum* adult males fed for 11 to 12 days (65 ticks; 2.39 mg proteins). FIG. 7 shows that the fractionated SGE contains at least two peaks of activity against the chemokines, one anti-IL-8 peak at fraction 41, and one anti-MIP-1α, RANTES, and MCP-1 peak at fraction 38. The results are consistent with those obtained for *D. reticulatus* (FIGS. 4 and 5), indicating the presence of at least one anti-CXC (IL-8) chemokine molecule and at least one anti-CC (MIP-1α, RANTES, MCP-1) chemokine molecule. However, differences in the activity profiles indicate inter-species variation in anti-chemokine molecules.

Example 6

Effect of Tick Saliva on Chemokines Levels

Figure 8:
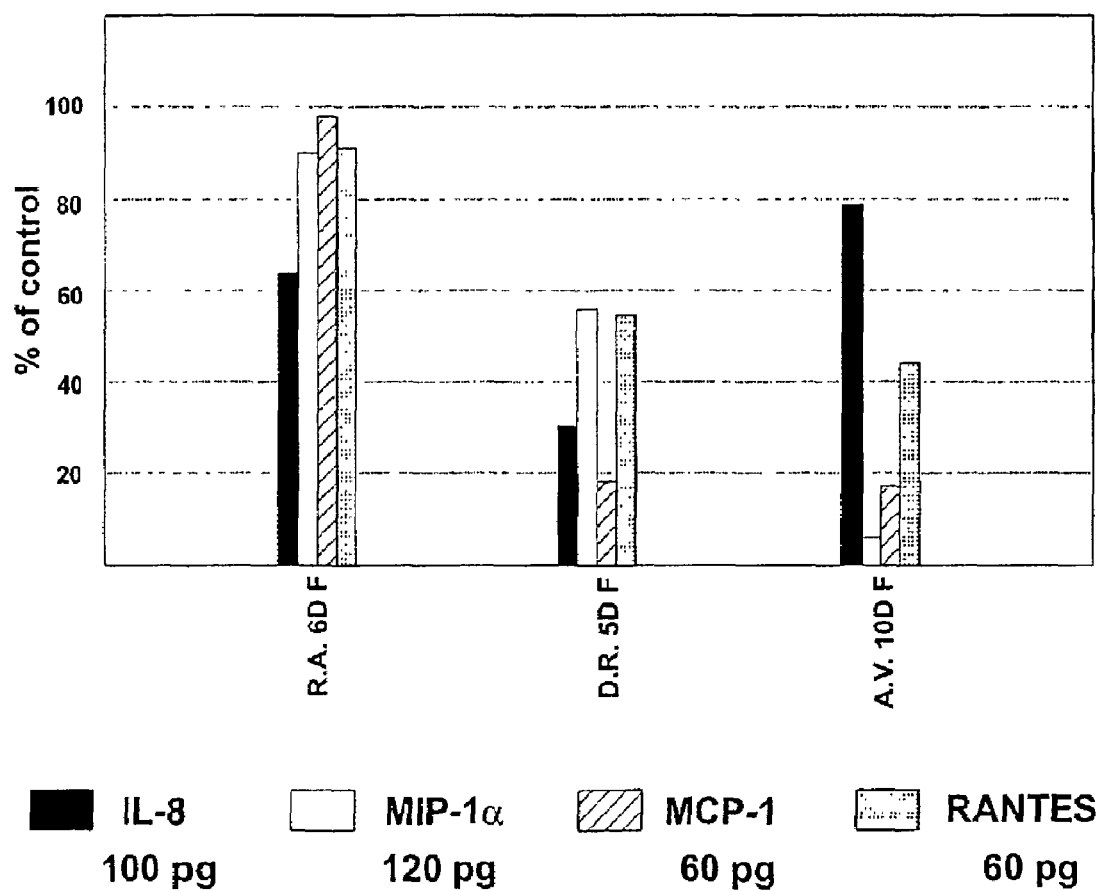
FIG. 8 shows the anti-chemokine activity of saliva from female: *Rhipicephalus appendiculatus* 10 ticks (15.0 µg protein) fed for 6 days (R.A.6D F), *Dermacentor reticulatus* 19 ticks (8.5 µg protein) fed for 5 days (D.R.5D F), *Amblyomma variegatum* 6 ticks (10.2 µg protein) fed for 10 days (A.V.10D F). ELISA results are shown as % optical density in the presence of saliva compared with the control (chemokine not treated with saliva).

The method used in Example 3 was repeated using saliva from female *R. appendiculatus* 10 ticks (15.0 µg protein) fed for 6 days, *D. reticulatus* 19 ticks (8.5 µg protein) fed for 5 days, or *A. variegatum* 6 ticks (10.2 µg protein) fed for 10 days. FIG. 8 shows that the anti-chemokine activity of saliva from the different tick species matched the results obtained using fractionated SGE (FIGS. 4-7). Saliva from *R. appendiculatus* showed activity against IL-8 but not against the other chemokines tested whereas saliva from *D. reticulatus* and *A. variegatum* inhibited all four chemokines to varying degrees. Saliva from *D. reticulatus* appeared to be particularly potent against IL-8 and MCP-1 while saliva of *A. variegatum* was relatively most potent against MIP-1α.

Example 7

Effect of FPLC Fractions of *A. variegatum* and *D. reticulatus* SGE on the Level of Eotaxin The method used in Example 3 was repeated using the FPLC fractions of SGE from male ticks of either *A. variegatum* or *D. reticulatus*. FIG. 9 shows a peak of anti-eotaxin activity for both *A. variegatum* or *D. reticulatus* which was similar to that observed with MIP-1α (FIGS. 7 and 5, respectively). The results are consistent with detection of at least one anti-CC chemokine molecule.

Example 8

Effect of FPLC Fractions of *D. reticulatus* SGE on the Level of IP-10

Figure 10:
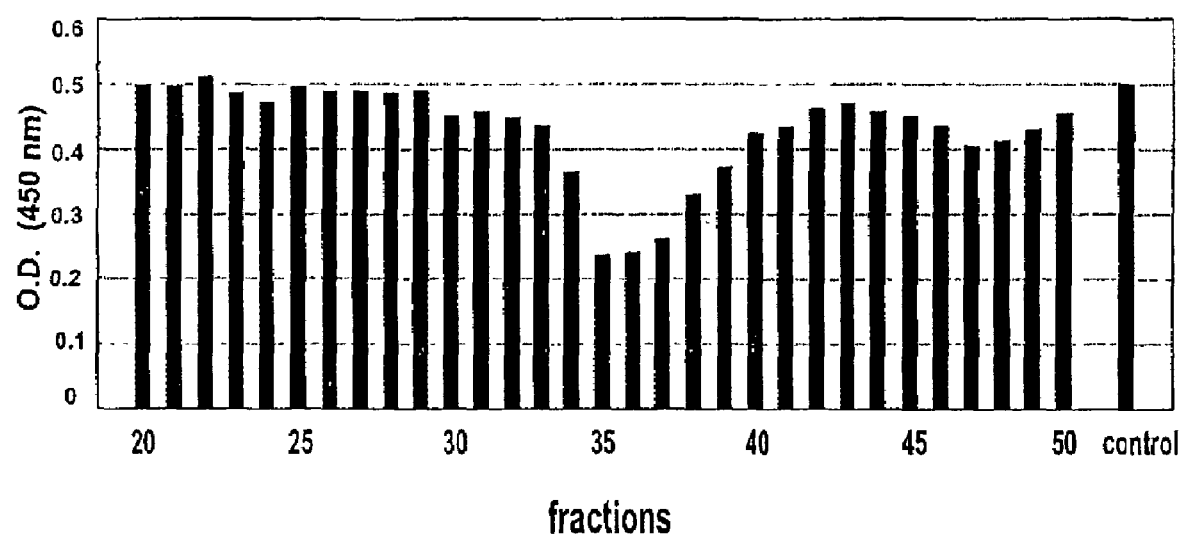
FIG. 10 shows the anti-IP-10 activity of FPLC fractions (1 µl) of SGE derived from 5 to 6 days fed Dermacentor male ticks using 60 pg IP-10 per treatment detected by ELISA.

The method used in Example 3 was repeated using the FPLC fractions of SGE from male ticks of *D. reticulatus* fed for 5-6 days. FIG. 10 shows a peak of anti-IP-10 activity which was similar to the higher molecular weight peak observed with IL-8 (FIG. 5). The result is consistent with detection of at least one anti-CXC chemokine molecule.

Example 9

Effect of Trypsin Treatment of *D. reticulatus* SGE on Chemokine Levels.

Figure 11:
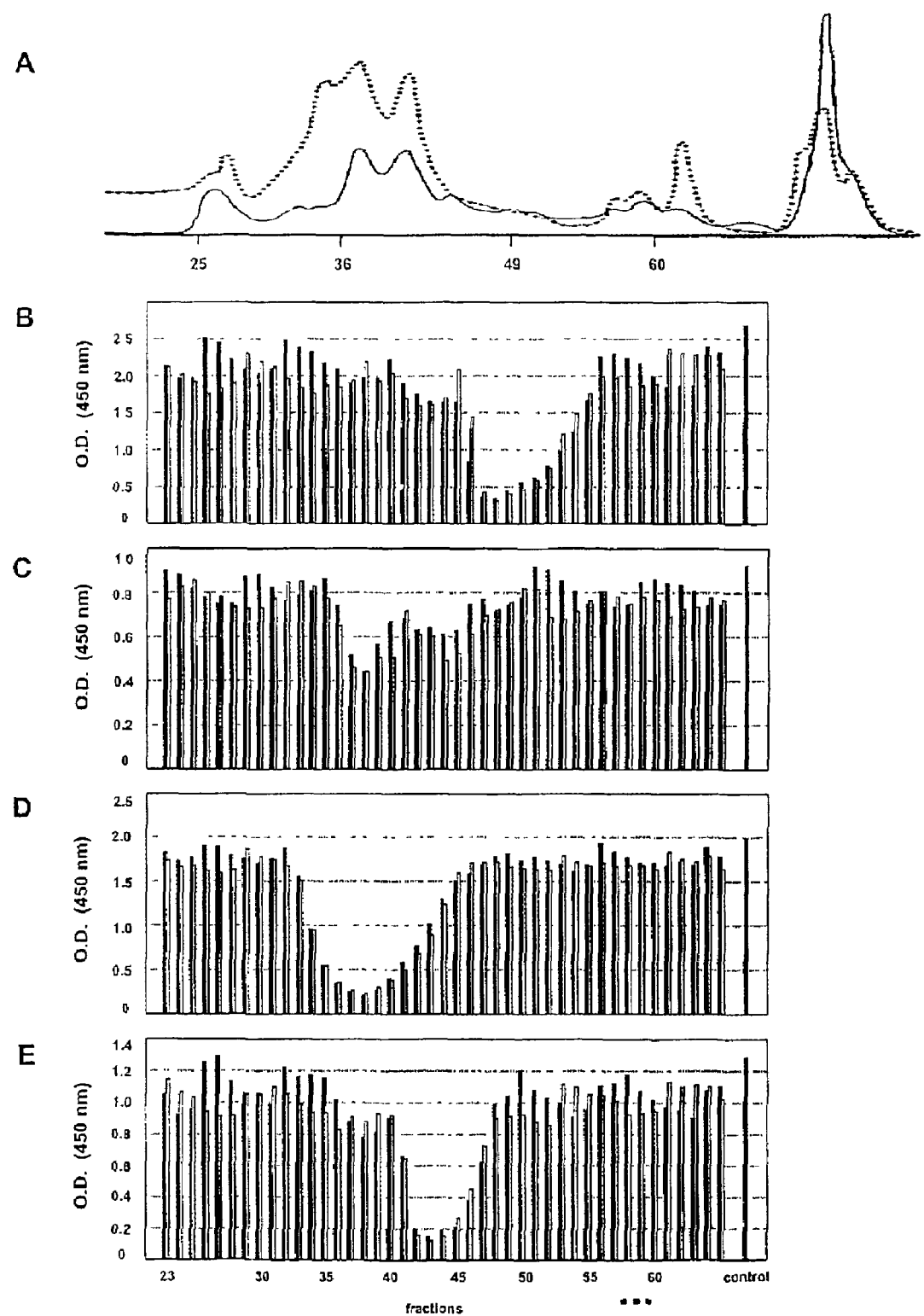
FIG. 11 shows the effect of trypsin treatment of SGE derived from 5 days fed *Dermacentor reticulatus* female ticks: (A) on the total protein profile (broken line untreated, continuous line after trypsin treatment), and (B-E) on the anti-chemokine activity of FPLC fractions from the SGE either treated with trypsin (◐) or untreated (■), detected by ELISA.

SGE of female *D. reticulatus* fed for 5 days was treated with trypsin (or untreated as the control) and then fractionated by FPLC, and the fractions tested by ELISA for anti-chemokine activity. FIG. 11A shows that trypsin treatment resulted in protein digestion, reducing the size of proteins with a resulting change in protein profile. However, FIGS. 11B to 11E show that the anti-chemokine activity profiles of FPLC fractions of SGE treated with trypsin (□) were similar to those for untreated SGE (■). The results indicate that the tick anti-chemokine molecules are resistant to trypsin digestion, a property characteristic of (but not unique to) proteoglycans.

Example 10

Effect of Protease Inhibitors of the Action of Tick SGE on IL-8

Tablets of an EDTA-free protease inhibitor cocktail (Boehringer Mannheim GmbH, Germany) were each dissolved in 2 ml water. The metalloproteinase inhibitor, ethylenediaminetetraacetic acid (EDTA) disodium salt (SIGMA) was used at a final concentration of 5 mM.

Ten µl SGE were mixed with 10 µl protease inhibitor. For the protease inhibitor cocktail, after 15 min incubation, IL-8 was added and after a further 2 hr incubation, the level of IL-8 was determined by ELISA. For EDTA treatment, SGE and the inhibitor were incubated for 1 hr before IL-8 was added for a further 1 hr prior to ELISA.

Figure 12:
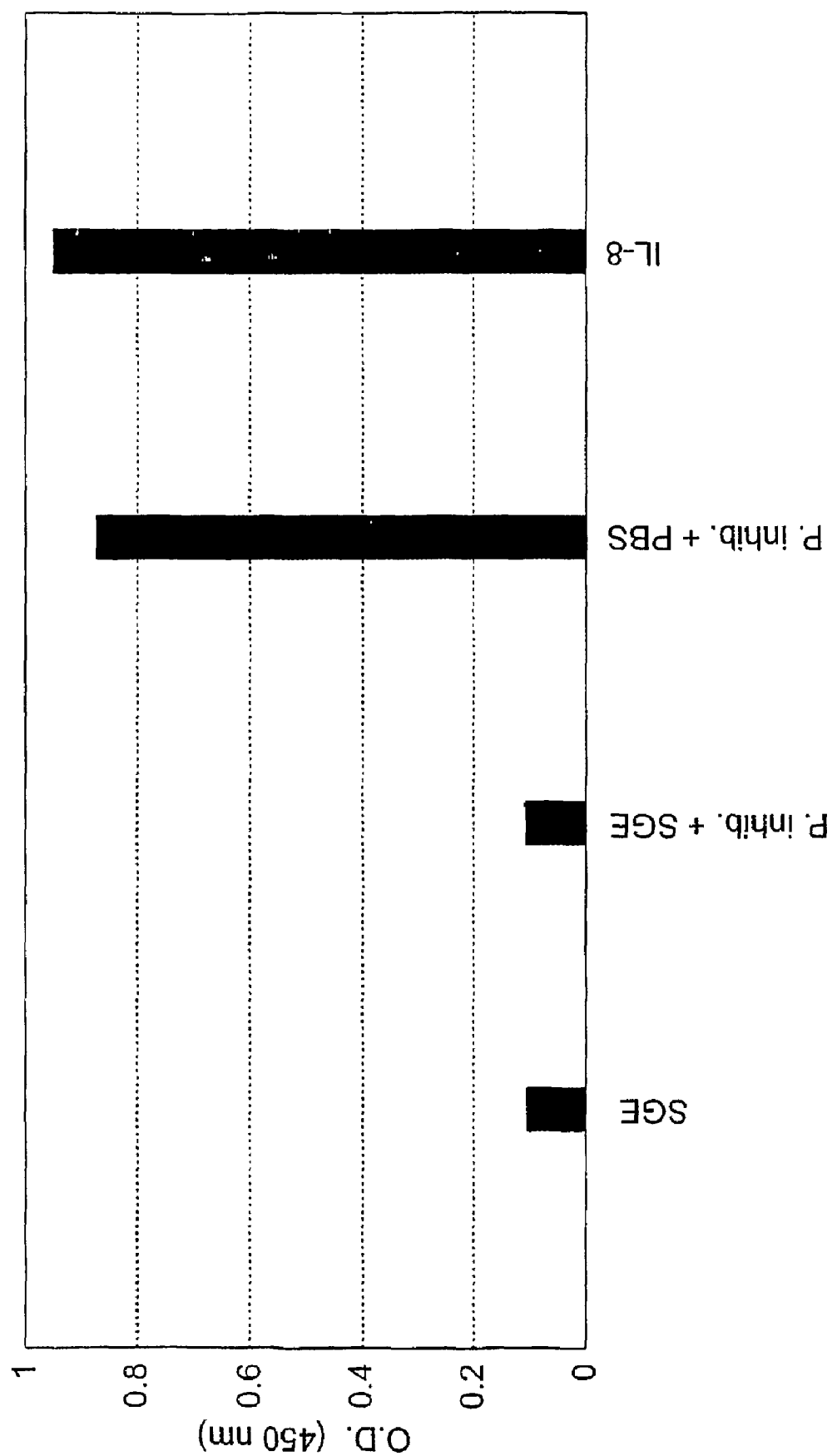
FIG. 12 shows the detection by ELISA of IL-8 after incubation with *D. reticulatus* SGE pretreated with a protease inhibitor cocktail. P. inhib.=protease inhibitor; PBS=phosphate buffered saline (control).

The protease inhibitor cocktail affected neither the amount of IL-8 in the absence of SGE (control) nor the decrease in IL-8+SGE, indicating that the anti-IL-8 effect of the SGE was not due to proteolytic activity (FIG. 12).

Figure 13:
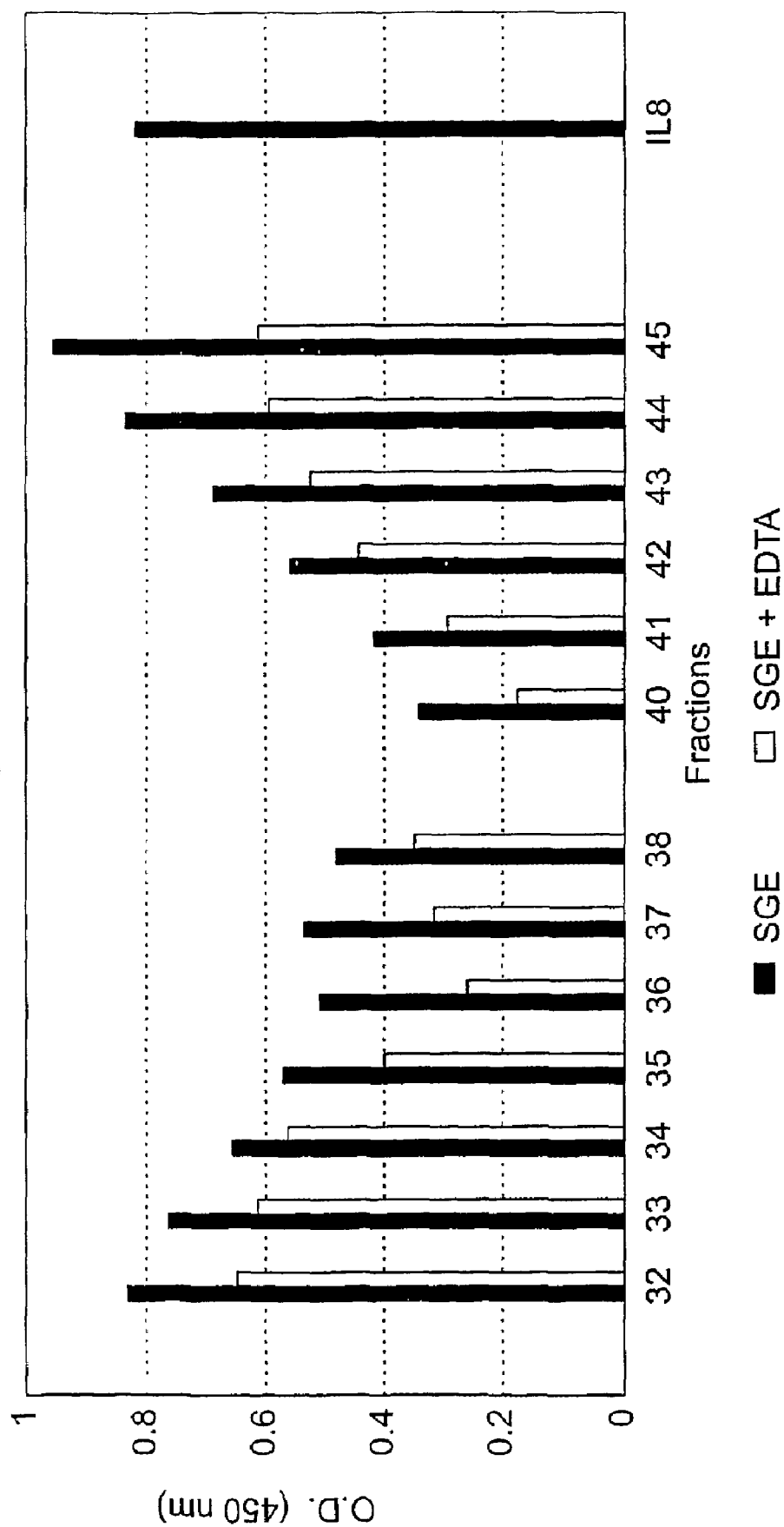
FIG. 13 shows the detection by ELISA of 100 pg of IL-8 after incubation with FPLC fractions of SGE derived from *D. reticulatus* adult females that were either untreated (SGE) or treated with the metalloproteinase inhibitor, ethylene diamine tetraacetic acid (SGE+EDTA).

FIG. 13 shows that anti-IL-8 activity remained following treatment with EDTA indicating that anti-IL-8 activity is not due to the action of a metalloproteinase in tick SGE.

Example 11

Binding of $I^{125}$-IL-8 to Tick SGE

Human recombinant $^{125}I$/-Interleukin-8 was obtained from NEN Life Science Products, USA (Cat. No. NEX277); Immobilon-P transfer PVDF membranes from MILLIPORE, USA (Cat. No. IPVH 304 F0); and goat anti-human IL-8 IgG from Research Diagnostics Inc., USA (Cat. No. RDI-IL8 abgX). One mg of the goat antibody was dissolved in 1 ml of sterile distilled water and stored in aliquots of 10 µl at −70° C.

Drops (5 to 10 µl) of samples (SGE, FPLC fractions of SGE, anti-IL-8 antibodies) were allowed to absorb 45 mins at 4° C. to pre-wetted membranes. Membranes were washed in 50 ml TTBS (20 mM Tris-HCl, 500 mM NaCl, 0.05% Tween-20, pH 7.5) for 10 min and unoccupied sites on the membranes were saturated with 15 ml TTBS+3% bovine serum albumin (BSA) for 1 hr at room temperature. Then membranes were washed in 40 ml of TTBS (for 10 mins plus two times for 5 mins) and incubated in 5 ml of TTBS pH 8+100 µl $^{125}I$-IL-8 for 90 mins at room temperature by gentle shaking. Finally, membranes were washed again in 30 ml TTBS (1× for 10 mins and 5× for 5 mins), dried and then exposed 3-4 days to X-ray film (CRONEX, DU PONT).

Figure 14:
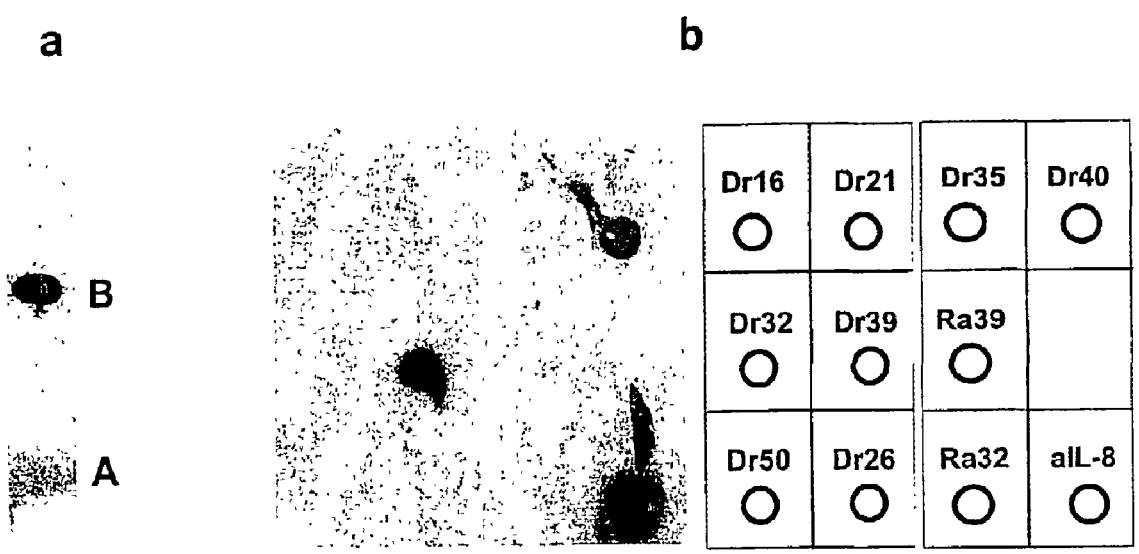
FIG. 14 shows the binding of $^{125}$I-IL-8 to: (a) SGE of *D. reticulatus* adult females fed for 5 days (A) and anti-IL-8 antibody (B) as a positive control; (b) selected FPLC fractions of different ticks species (shown in left hand panels) as indicated (shown in right hand panels)—Dr16, Dr21, Dr32, Dr39, Dr50, Dr26, Dr35, Dr40, are the indicated fractions from *D. reticulatus* female ticks fed for 5 days and Ra39, Ra32, are the indicated fractions from *R. appendiculatus* female ticks fed for 5 days, aIL-8 is goat anti-IL-8 antibody (positive control).

Samples were dot-blotted onto the membranes, in volumes of either 5 µl (aA, Dr16, Dr21, Dr32, Dr39, Dr50, Dr26) or 10 µl (aB, Dr35, Dr40, Ra39, Ra32, aIL-8). In FIG. 14a, the radiolabelling of SGE treated with $^{125}$IL-8 indicates that anti-IL-8 activity is due to a molecule(s) in tick SGE that binds IL-8. The results shown in FIG. 14b indicate that *D. reticulatus* FPLC fraction 39 has very strong IL-8 binding activity. Binding activity was also shown by *D. reticulatus* fraction 40, and weak binding by fraction 35. The other fractions did not show binding activity.

Example 12

Cross-linking of $I^{125}$-IL-8 to Tick SGE

Sodium dodecyl suphate-polyacrylamide gel electrophoresis (SDS-PAGE) with discontinuous buffers was carried out in a gradient of 7.5 to 12.5% polyacrylamide in 1.5 mm thick gels (Laemmli, 1979) in reducing or non-reducing conditions (with or without β-mercaptoethanol, respectively).

FPLC fractions of SGE were dialysed in PBS for 1 hr. Two µl of $^{125}I$-IL8 were added to 30 µl of either the FPLC fraction or PBS. Then, 1.6 µl of either the stock solution of crosslinker, dithiobis sulfosuccinimidylpropionate (DTSS) from Pierce (1.7 mg of DTSSP dissolved in 0.139 ml PBS at a 20 mM concentration) prepared just prior to use, or PBS were added to the samples. Final concentration of DTSSP was 1 mM in the reaction mixture. Samples were incubated for 30 mins at room temperature. The crosslinking reaction was quenched for 15 mins by adding 1.1 µl of TRIS solution pH 7.5 at a final concentration of 30 mM in the reaction mixture.

Crosslinked products were observed (FIG. 15) with a band in fraction 35 running at approximately 30 to 40 kD and a band in fraction 41 of approximately 14 to 20 kD.

The results shown in FIG. 15 confirm that a molecule(s) in SGE binds to IL-8.

Example 13

Binding of $I^{125}$-IL-8 to FPLC Fraction 40 of *D. reticulatus*

Fraction 40 was resolved by SDS-PAGE gel electrophoresis. The gel was electroblotted onto PVDF membranes in Towbin transfer buffer (25 mM Tris, 192 mM glycine, 20% methanol, pH 8.3) at 30 V and 100 mA for 16 hr at 10° C.

Figure 16:
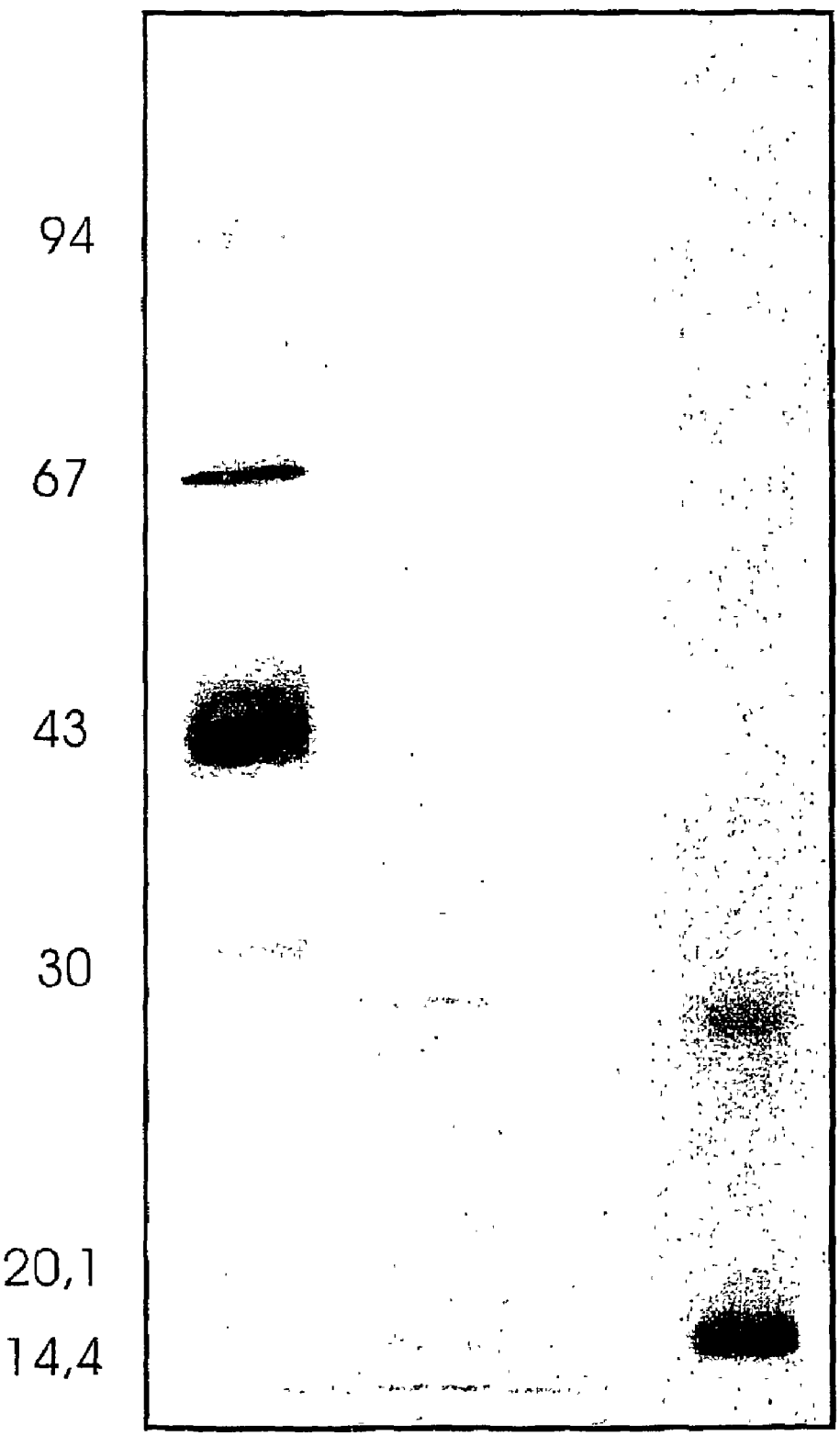
FIG. 16 shows SDS-PAGE of FPLC fraction 40 of SGE derived from *D. reticulatus* adult females run under non-reducing conditions. M.W.=molecular weight markers and track (A) are silver stained SDS-polyacrylamide gels and (B) shows $^{125}$I-IL-8 binding following electroblotting onto a PVDF membrane.

Both bands migrating at approximately 10-18 kD and the band of approximately 25-30 kD show strong binding of $^{125}I$-IL-8 (FIG. 16).

The results shown in FIG. 16 are a further indication that anti-IL-8 activity is due to an SGE molecule(s) that binds IL-8.

Example 14

Inhibition by Tick SGE of IL-8 Binding to the IL-8 Cell Receptor

Ten ml of fresh human blood were collected in a tube with 10 µl of heparin (5×10³ U/1 ml; Léciva Praha) and diluted 1:1 in 0.9% NaCl solution. Cell suspension was resuspended in 24 ml of deionised water for 30 sec to lyse erythrocytes, then 8 ml of 3.6% NaCl solution were added and the cells were centrifuged at 1000 rpm (K 23) for 10 min. The cell pellet was washed with 0.9% NaCl solution and centrifuged at 1000 rpm (K 23, Janetzki) for 10 min. Cells were resuspended in 2 ml RPMI supplemented with 10% FCS. Cell number was determined using Türk's solution and diluted to 4×10⁶ and/or 2×10⁶ granulocytes per milliliter.

SGE from *D. reticulatus* adult females fed for 5 days was diluted in 50 µl of PBS at a final concentration 50 µg and/or 10 µg and/or 5 µg. Ten µl of each fraction were diluted in 40 µl of PBS. IL-8 was used in the assay at a final concentration 50 ng in 50 µl of either PBS or solution of SGE. 1.2 µl of $^{125}I$-IL8 was diluted in 50 µl of either PBS or solution of either SGE or fraction.

For the radioassay, mixtures of $^{125}I$-IL8 with either SGE or FPLC fraction or PBS (control) were incubated for 1 hour at room temperature. The mixtures were then added to cells (200,000 per well) and incubated for 1 hour at room temp. Cell suspensions were 3 times washed with PBS. Pellets of cells were resuspended in 50 µl PBS and measured using a gammacounter. To demonstrate specific binding (competition of radiolabelled and unlabelled IL-8), cells were pretreated for 30 min with unlabelled IL-8.

Figure 17:
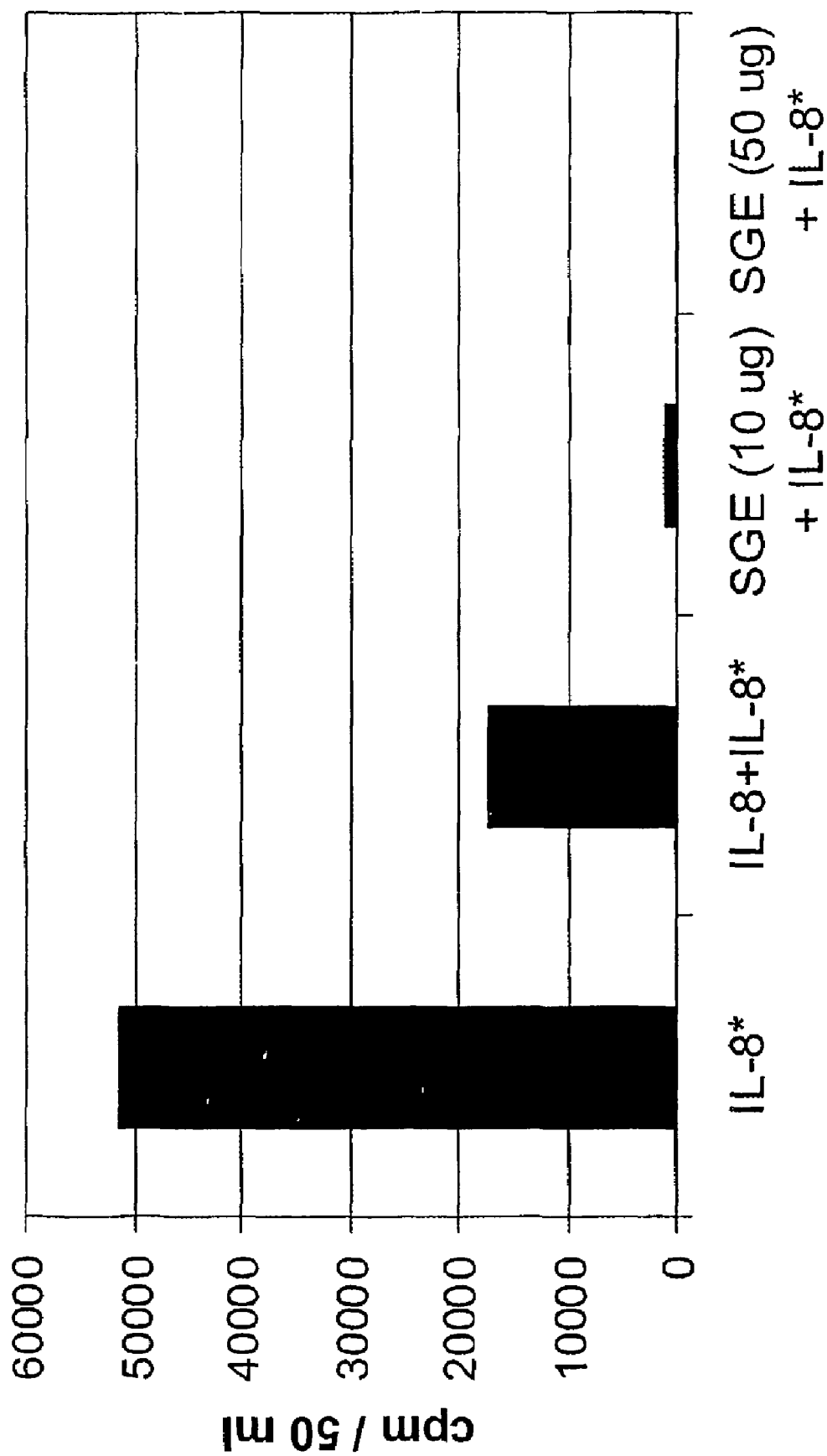
FIG. 17 shows the inhibition by tick SGE of $^{125}$I-IL-8 binding to its cell receptor. IL-8*=$^{125}$I-IL-8 binding to its receptor; IL-8+$^{125}$I-IL-8=radiolabelled IL-8 bound to its receptor in the presence of cold (unlabelled) IL-8; SGE (10 µg)+$^{125}$I-IL-8=radiolabelled IL-8 bound to its receptor when treated with 10 µg of tick SGE; SGE (50 µg)+$^{125}$I-IL-8=radiolabelled IL-8 bound to its receptor when treated with 50 µg of tick SGE. SGE was from *D. reticulatus* adult females fed for 5 days.

FIG. 17 shows the inhibition by tick SGE of $^{125}$I-IL-8 binding to its cell receptor. When the cells were pretreated with cold (unlabelled) IL-8, the amount of $^{125}$I-IL8 binding to its receptor was reduced, indicating the specificity of receptor binding. When $^{125}$I-IL8 was treated with either 10 µg or 50 µg SGE, there was a substantial dose dependent reduction in binding of the radiolabelled IL-8 to its receptor, indicating that anti-IL-8 activity is due a molecule(s) in SGE that binds to IL-8 and thereby prevents IL-8 binding to its receptor.

Figure 18:
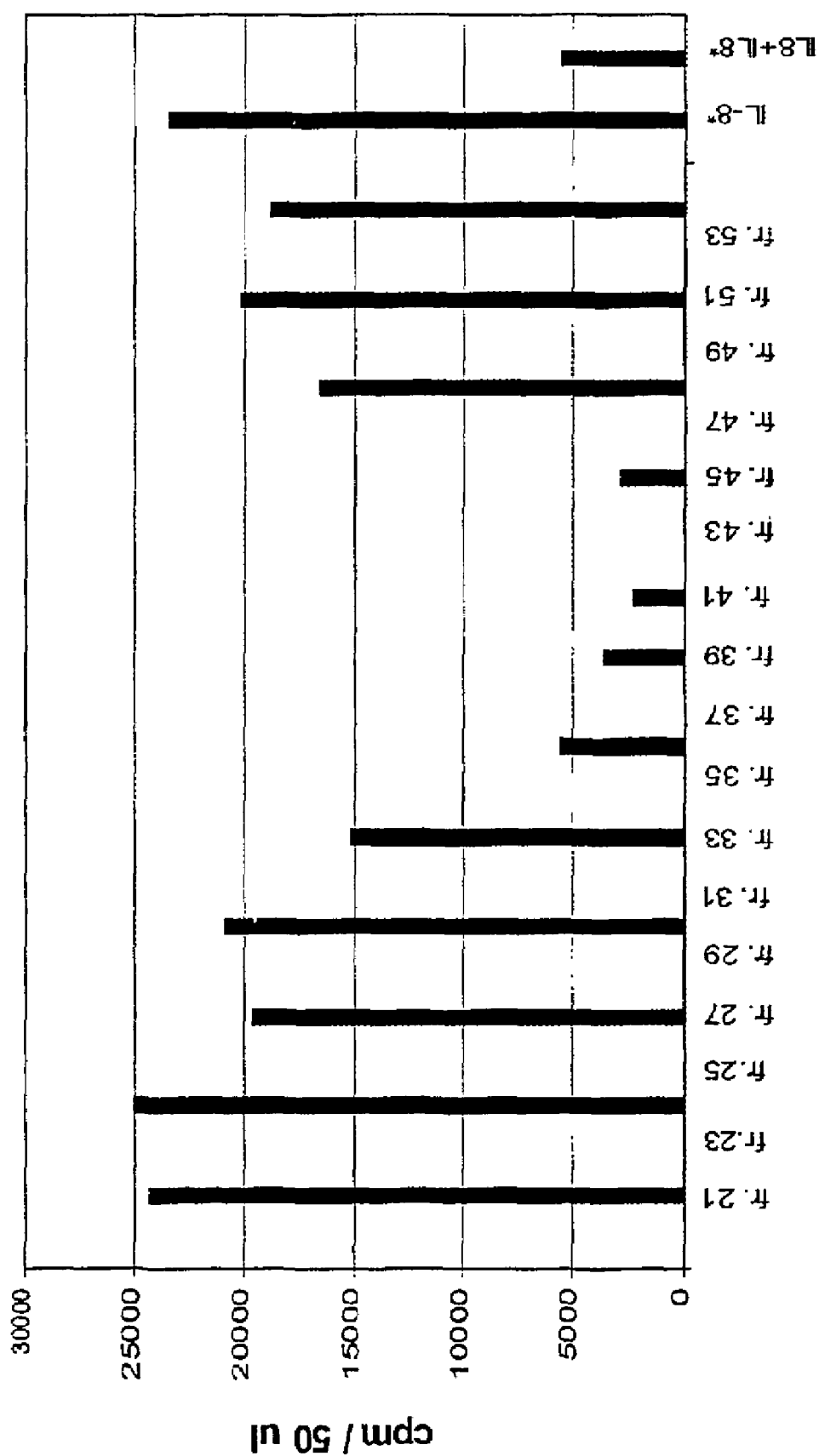
FIG. 18 shows the inhibition of $^{125}$I-IL-8 binding to its cell receptor by FPLC fractions of tick SGE. IL-8*=$^{125}$I-IL-8 binding to its receptor; IL-8+$^{125}$I-IL-8=radiolabelled IL-8 bound to its receptor in the presence of cold (unlabelled) IL-8; fr.xx=radiolabelled IL-8 bound to its receptor when treated with fraction as numbered. SGE is from *D. reticulatus* adult females fed for 5 days.

When the assay was repeated using FPLC fractions of SGE from *D. reticulatus* adult females fed for 5 days, peak inhibition of IL-8 binding to its receptor occurred when IL-8 was treated with fractions 36 to 45 (FIG. 18). The results are in accordance with those obtained using ELISA (Example 3).

Example 15

Inhibition by Tick SGE of IL-8 Chemotactic Activity

Agarose plates were prepared according to the method of van Damme and Cunings (1995). Solution A comprised 2 ml foetal calf serum (FCS, Biocom), 2 ml 10× concentrated Eagle's minimum essential medium (EMEM, Sigma) with Earle's salts, L-glutamine and sodium-bicarbonate, and 6 ml distilled water. The medium was pre-warmed to 50° C. Solution B comprised 0.18 g agarose (Indubiose, IBF) boiled in 10 ml distilled water until completely dissolved and cooled to 50° C. Solutions A and B were then mixed in equal volumes and poured into 3 plastic tissue culture dishes (6 ml per 1 dish Ø 6 cm) and were allowed to cool. The dishes were transferred to a refrigerator (4° C.) until further processing. Immediately before the chemotaxis assay, a series of six rows (per dish) of three wells were made using a punch and vacuum.

Granulocytes were isolated from human peripheral blood using a modification of the method described by van Damme and Cunings (1995). Briefly, 10 to 15 ml fresh human blood were collected in a tube with heparin and diluted 1:1 in 0.9% NaCl solution. The cell suspension was carefully loaded onto a 10 ml mixture of Ficol-Telebrix (d=1.077-1.079) and centrifuged at 1300 rpm (K 80) for 50 min. The second layer consisting of erythrocytes and granulocytes was washed 3 times with 0.9% NaCl solution and centrifuged at 1000 rpm for 10 min. The cell pellet was resuspended in 24 ml of deionised water for 30 sec to lyse the erythrocytes, and then 8 ml of 3.6% NaCl solution was added and the cells were centrifuged at 1000 rpm for 10 min. The cell pellet was washed with 0.9% NaCl solution and centrifuged at 1000 rpm for 10 min. Cells were resuspended in 1 ml EMEM supplemented with 5% FCS. Cell number was determined using Türk's solution and diluted to $3 \times 10^7$ granulocytes per milliliter.

Ten µl IL-8 ($3 \times 10^4$ U/10 µl kindly supplied by Prof. Arden, Belgium) were mixed with either 10 µl SGE (45 µg total protein), or 10 µl of each test FPLC fraction. The controls were 10 µl IL-8 mixed with 10 µl or either antibody (2 mg/1 ml) or phosphate-buffered saline (PBS). All the samples were incubated for 30 min at 37° C. in a humidified $CO_2$ (5%) incubator.

For the chemotaxis assay, 10 µl of non-chemotactic medium (negative control) were added to the outer well of each series of three wells. 10 µl of either diluted test sample or standard were added to the inner well. Formylmethionyl-leucylphenylalanine (FMLP) at $10^{-6}$ M was used as a positive control. The centre well of each series of three wells was filled with 10 µl of cells, e.g. $3 \times 10^5$ granulocytes. Agarose plates were incubated for 2 hr at 37° C. in a humidified $CO_2$ (5%) incubator. The assay was terminated by adding absolute methanol (3 ml per dish) to the agarose plates for 30 min at room temperature. The methanol was carefully decanted and the cells were fixed with formaldehyde (3 ml per dish) for 30 min. The agarose was carefully removed from the culture dish and the cells were stained with May-Grünwald's solution (5 ml per dish) for 10 min and Giemsa's solution (5 ml per dish) for 20 min.

Figure 19:
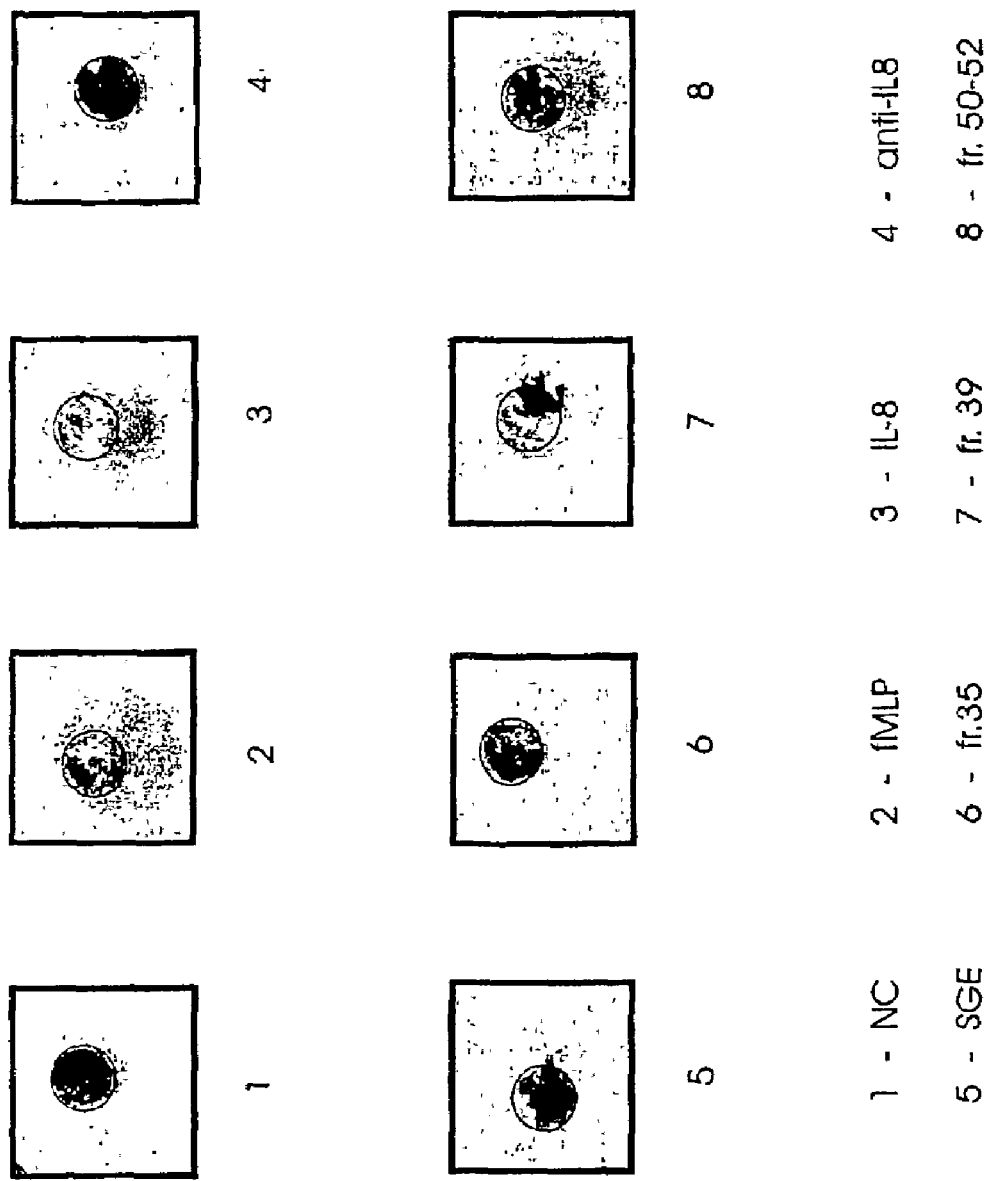
FIG. 19 shows inhibition by tick SGE of the chemotactic activity of IL-8. NC=untreated cells (negative control); fMLP $10^{-6}$ =formylmethionyl-leucylphenylalanine at $10^{-6}$ M (positive control of chemotaxis); IL-8 50,000 U=demonstration of chemotactic activity of IL-8; IL-8+anti-IL-8=inhibition of chemotactic activity of IL-8 with specific antibodies; IL-8+SGD D.R.=IL-8 treated with *D. reticulatus* SGE; IL-8+fr. 35=IL-8 treated with FPLC fraction 35 of *D. reticulatus* SGE; IL-8+fr. 39=IL-8 treated with FPLC fraction 39 of *D. reticulatus* SGE; IL-8+fr. 50-52=IL-8 treated with FPLC fractions 50 to 52 of *D. reticulatus* SGE.

The results (FIG. 19) show that the chemotactic action of IL-8 was inhibited when IL-8 was treated with either anti-IL-8 antibodies (control), or with SGE derived from *D. reticulatus* adult females fed for 5 days or FPLC fraction 35 or 39. By contrast, IL-6 chemotactic activity was unaffected by the treatment of IL-8 with a mixture of FPLC fractions 50-52. These results show that the anti-IL-8 activity of SGE detected in the preceding examples was able to inhibit the biological activity (i.e. chemotaxis) of IL-8.

Example 16

Isolation of Anti-chemokine Molecules Using Proteomics 2D gel electrophoresis resolved the protein components of *D. reticulatus* and *A. variegatum* female SGE (FIGS. 20A and 20F, respectively) and *A. variegatum* female saliva (FIG. 20E). Comparison of the 2D gels of IL-8 binding and non-binding fractions (FIGS. 20B and 20D compared with FIG. 20C) identified two candidates for the IL-8 binding activity shown in FIG. 16 of approximately 15 kD.

REFERENCES

Alcami et al (1995) Pox viruses: capturing cytokines and chemokines. *Seminars in Virology* 5: 419-427.

Alcami, A. and Smith, G. L. (1995). Cytokine receptors encoded by pox viruses: a lesson in cytokine biology. *Immunology Today* 16: 474-478.

Anderson, R. M. and May, R. M. (1991). Infectious Diseases of Humans. Dynamics and Control. Oxford University Press. 757 pp.

Ausubel E. A. et al Current Protocols in Molecular Biology, Wiley Interscience, New York.

Bradford, M. M. (1976). A rapid and sensitive method for the quantitation of microgram quantities of protein utilizing the principle of protein-dye binding. *Analytical Biochemistry* 72:248-254.

Cook, D. N., (1996) The role of MIP-1-alpha in inflammation and haematopoiesis *J. Leuk. Biol.* 59: 61-67

Dunbar, B. S. (1987). Two-dimensional electrophoresis and immunological techniques, pp. 217-221. New York: Plenum Press.

Fernandez J. M. & Hoeffler J. P., eds. (1998) Gene expression systems. Using nature for the art of expression. Academic Press, San Diego, London, Boston, New York, Sydney, Tokyo, Toronto.

Hajnicka et al (2000) Inhibition of the antiviral action of interferon by tick salivary gland extract. *J. Imm.* In press.

Harrada, A. et al., (1994) Essential involvement of interleukin-8 (IL-8) in acute inflammation. *J. Leuk. Biol.* 56: 559-564.

Jones, L. D. et al. (1988). The rearing and maintenance of ixodid and argasid ticks in the laboratory. *Animal Technol.* 39:99-106.

Kubeš, M., N. et al (1994) Salivary gland extracts of partially fed *Dermacentor reticulatus* ticks decrease natural killer cell activity in vitro. *Immunol.* 84:113-116.

Laemmli, U. K. (1979) Cleavage of structural proteins during the assembly of the head of bacteriophage T4. *Nature* 227:680-685.

Nuttall, P. A. et al (1994) Adaptations of arboviruses to ticks. *J. Med. Entomol.* 31:1-9.

Sambrook J. et al (1989) Molecular cloning: a laboratory manual New York: Cold Spring Harbour Laboratory Press.

Schwarz & Wells (1999a) Recent developments in modulating chemokine networks. *Exp. Opin. Ther. Patents* 9 (11): 1471-1490.

Schwarz & Wells (1999b) Interfering with chemokine networks—the hope for new therapeutics *Curr Opin. Chem. Biol.* 3: 407-417.

Spector et al (1998) Cells, a laboratory manual; Cold Spring Harbour Laboratory Press.

Van Damme, J. & Cunings, R. (1995) Assay for Chemotaxis. In: Cytokines, a Practical Approach Series, Ed. F. R. Balkwill, Chapter 13: 215-224.

Wikel, S. K., Ramachandra, R. N. and Bergman, D. K. (1994). Tick-induced modulation of the host immune response. *International Journal of Parasitology* 24: 59-66.

The invention claimed is:

1. A method of isolating a cytokine activity regulator molecule (CARM) derived from a an adult male or female tick comprising the steps of:
   a) preparing an extract from a the salivary gland of an adult male or female tick;
   b) separating said extract into fractions of differing molecular weight;
   c) testing said fractions for the ability to bind to and inhibit the activity of a cytokine, wherein said cytokine is a chemokine selected from the group consisting of IL-8, MIP-1α, MCP-1, RANTES, IP-10, and eotaxin; and
   d) isolating said CARM from a fraction(s) that possesses the ability to inhibit said cytokine activity.

2. A method according to according to claim 1 wherein preparation of said salivary gland extract takes place at a selected point in the feeding cycle of the adult male or female tick.

3. A method according to claim 2 wherein said adult male or female tick has been fed for 5 days or more.

4. A method according to claim 3 wherein said tick is from the species *Dermacentor reticulatus, Rhipicephalus appendiculatus, Amblyomma variegatum, Haemaphsalis inermis* or *Ixodes ricinus*.

5. A method according to claim 1 additionally comprising the step of sequencing said isolated CARM.

6. A method according to claim 1 wherein said isolating step (d) involves the use of a cytokine or cytokine receptor to identify and isolate the CARM.

7. A method according to claim 1 wherein the extract is separated into fractions by fast phase or high-performance liquid chromatography, or by SDS-polyacrylamide electrophoresis or two dimensional gel electrophoresis.

* * * * *